(12) United States Patent
Yoon et al.

(10) Patent No.: US 6,547,798 B1
(45) Date of Patent: Apr. 15, 2003

(54) RING APPLICATOR AND METHOD FOR APPLYING ELASTIC RINGS TO ANATOMICAL TISSUE STRUCTURES

(76) Inventors: InBae Yoon, 11886 Farside Rd., Ellicott City, MD (US) 21042; Ronald J. Brinkerhoff, 3030 Twin Ridge Dr., New Richmond, OH (US) 45157; Kendall L. Dobler, 1112 Black Horse Run, Cincinnati, OH (US) 45140; Hal H. Katz, 7903 Woodglen Dr., West Chester, OH (US) 45069; Ronald J. Kolata, 11316 Gedion La., Cincinnati, OH (US) 45249; William J. Kraimer, 8037 Buckland Dr., Cincinnati, OH (US) 45249; Leo J. Nolan, 10805 Clarion La., Las Vegas, NV (US) 89134; Delbert E. Lucas, 1270 Tolleywood Dr., Fairfield, OH (US) 45014; Donna R. Motz, 9638 Placid Dr., Cincinnati, OH (US) 45241

(*) Notice: Subject to any disclaimer, the term of this patent is extended or adjusted under 35 U.S.C. 154(b) by 0 days.

(21) Appl. No.: 09/563,912

(22) Filed: May 4, 2000

(51) Int. Cl.[7] ............................................. A61B 17/12
(52) U.S. Cl. ...................................... 606/141; 606/140
(58) Field of Search ................................ 606/139, 140, 606/141

(56) References Cited

U.S. PATENT DOCUMENTS

| | | | |
|---|---|---|---|
| 3,911,923 A | | 10/1975 | Yoon |
| 4,085,743 A | * | 4/1978 | Yoon |
| 4,167,188 A | | 9/1979 | Lay et al. |
| 4,226,239 A | | 10/1980 | Polk et al. |
| 4,230,116 A | | 10/1980 | Watson |
| 4,257,420 A | | 3/1981 | Terayama |
| 4,300,564 A | * | 11/1981 | Furihata |
| 4,374,523 A | | 2/1983 | Yoon |
| 4,471,766 A | | 9/1984 | Terayama |
| 4,485,814 A | | 12/1984 | Yoon |
| 4,493,319 A | | 1/1985 | Polk et al. |
| 4,548,201 A | | 10/1985 | Yoon |
| 5,569,268 A | * | 10/1996 | Hosoda ....................... 606/140 |
| 5,766,217 A | * | 6/1998 | Christy ....................... 606/148 |

* cited by examiner

Primary Examiner—Cary E. O'Connor
(74) Attorney, Agent, or Firm—The Law Offices of Royal Craig

(57) ABSTRACT

A ring applicator for applying elastic rings to anatomical tissue during surgical procedures includes an inner member with a forceps movably disposed within a middle tubular member having a distal end configured to hold a plurality of elastic rings in an expanded state and a proximal end with a plurality of longitudinally spaced steps. The middle tubular member is movably disposed in an outer tubular member, and an adjustable stop mechanism is mounted on the proximal end of the outer tubular member to limit axial movement of the outer tubular member relative to the middle tubular member to select which rings are to be ejected. A distal handle is connected with the inner member via slots in the outer and middle tubular members, and a proximal handle is pivotally connected to the middle tubular member via a slot in the outer tubular member. A pusher has a distal end movable between a latched or locked position where the distal end of the pusher protrudes into apertures in the outer and middle tubular members to prevent pivotal movement of the proximal handle and an unlatched or unlocked position where the distal end of the pusher is disengaged from the aperture in the middle tubular member to permit pivotal movement of the proximal handle in order to move the outer tubular member axially relative to the middle tubular member to eject an elastic ring. Distal portions of the outer and middle tubular members are preferably transparent with scale markings formed thereon to allow the surgeon to accurately determine the length of the tissue disposed within the middle tubular member prior to ejecting a ring. A prerelease feature is also disclosed for unlocking the pusher to allow ejection of a ring when the forceps has not been completely withdrawn in to the middle tubular member.

40 Claims, 12 Drawing Sheets

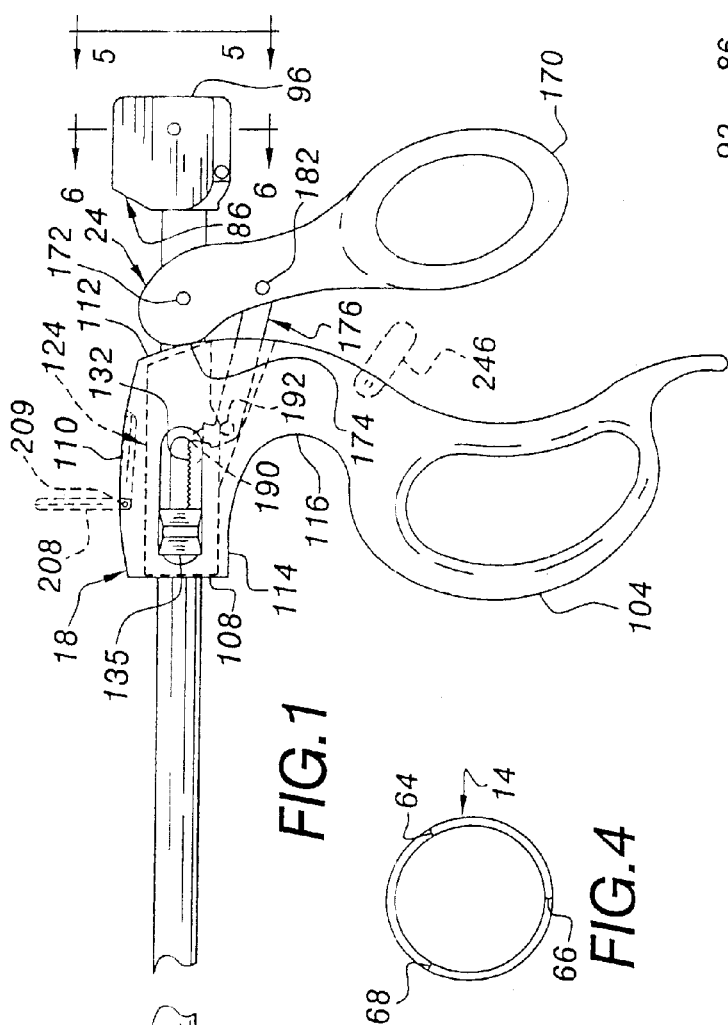
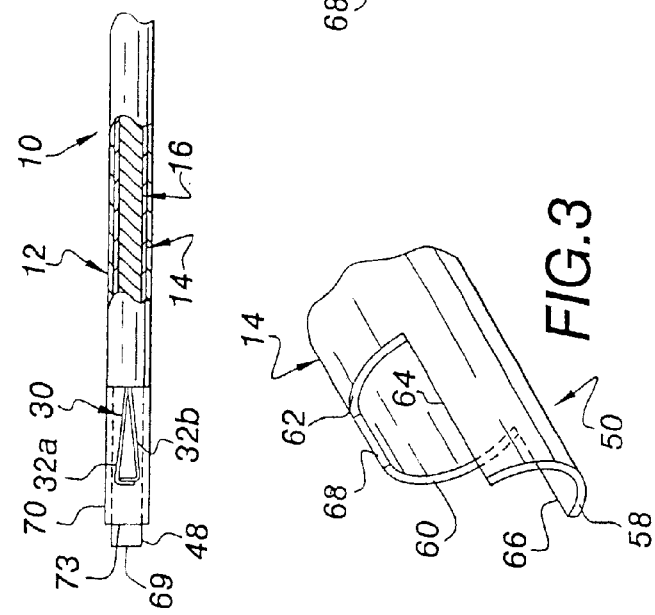
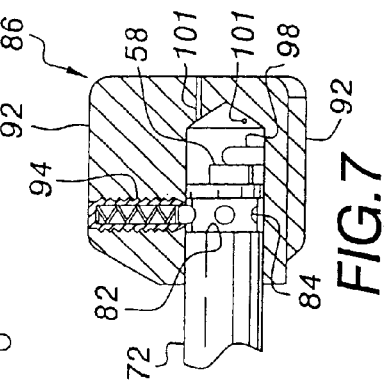
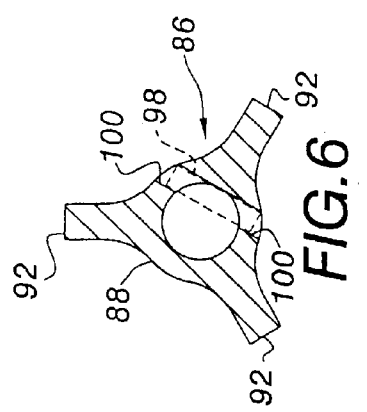
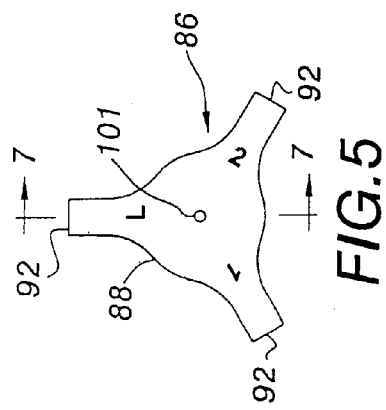

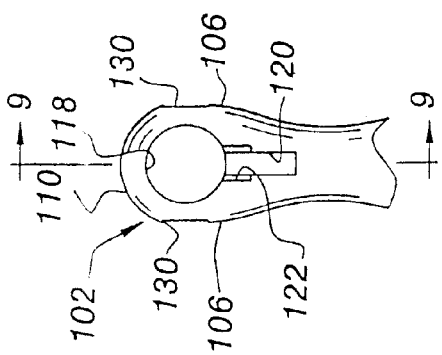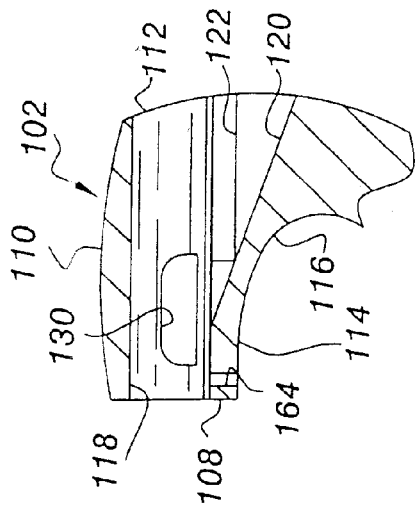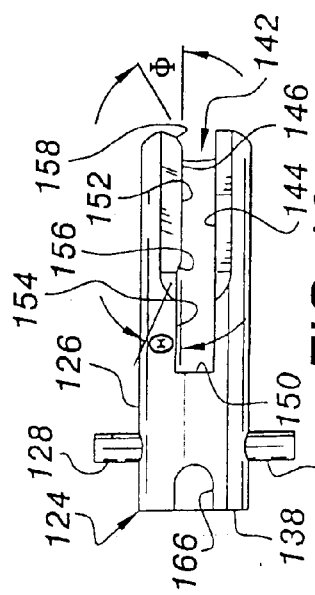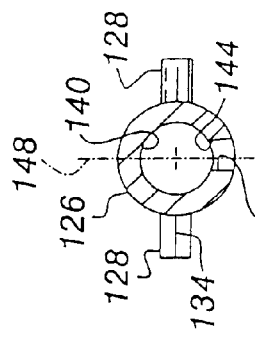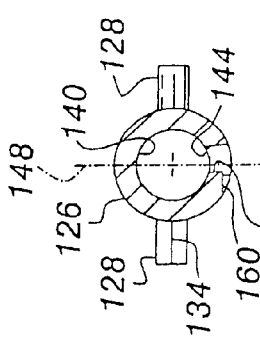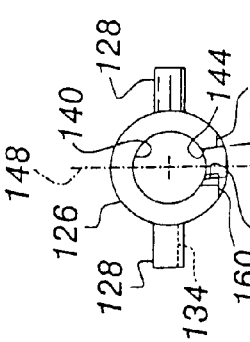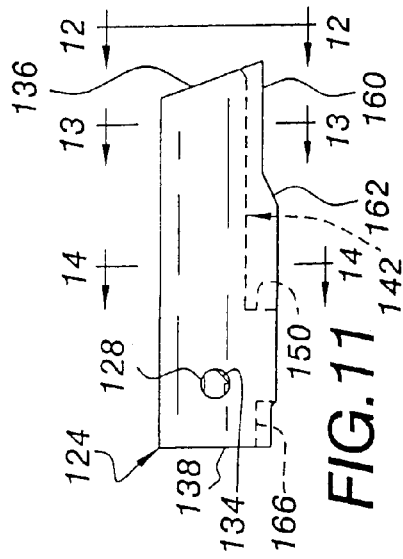

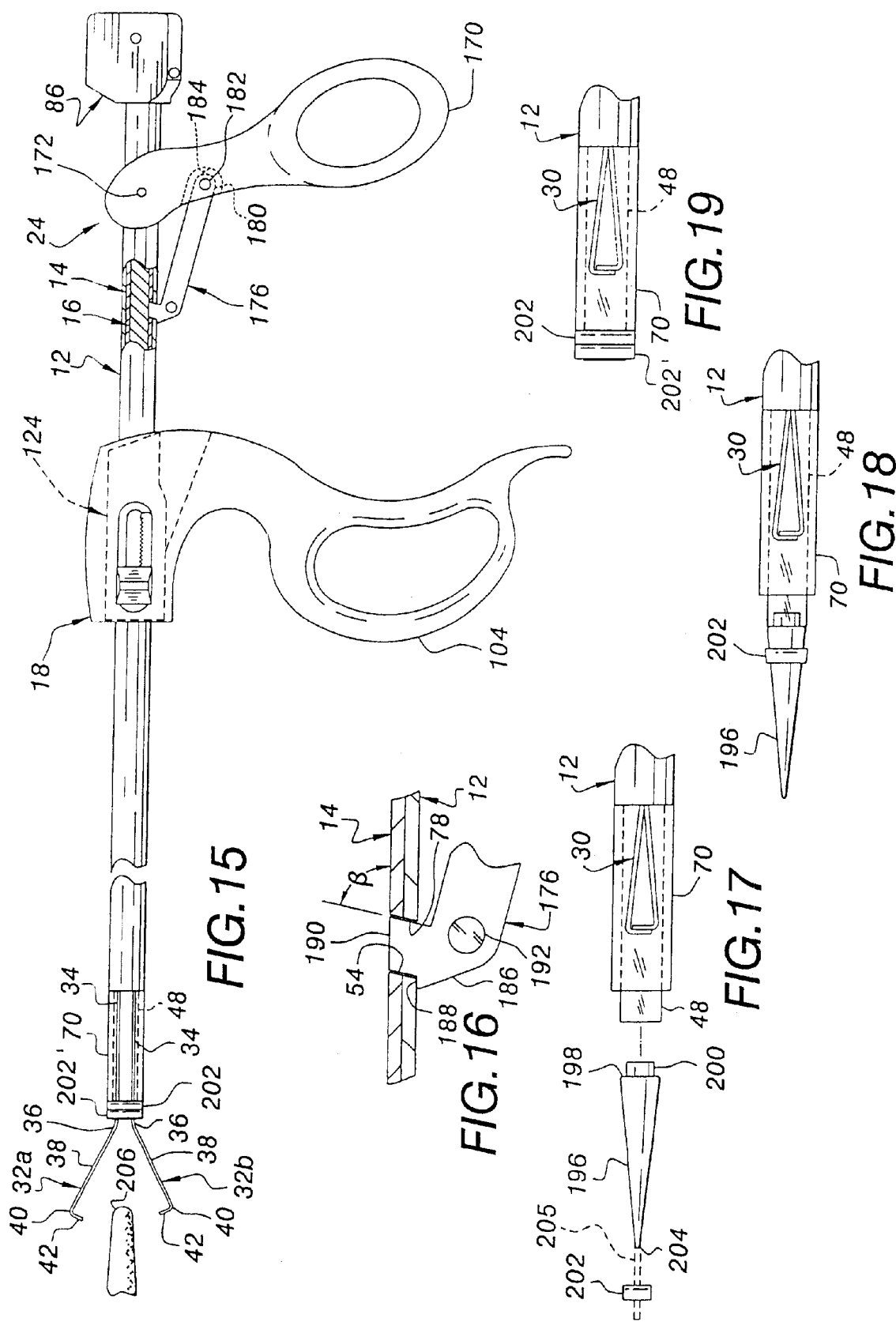

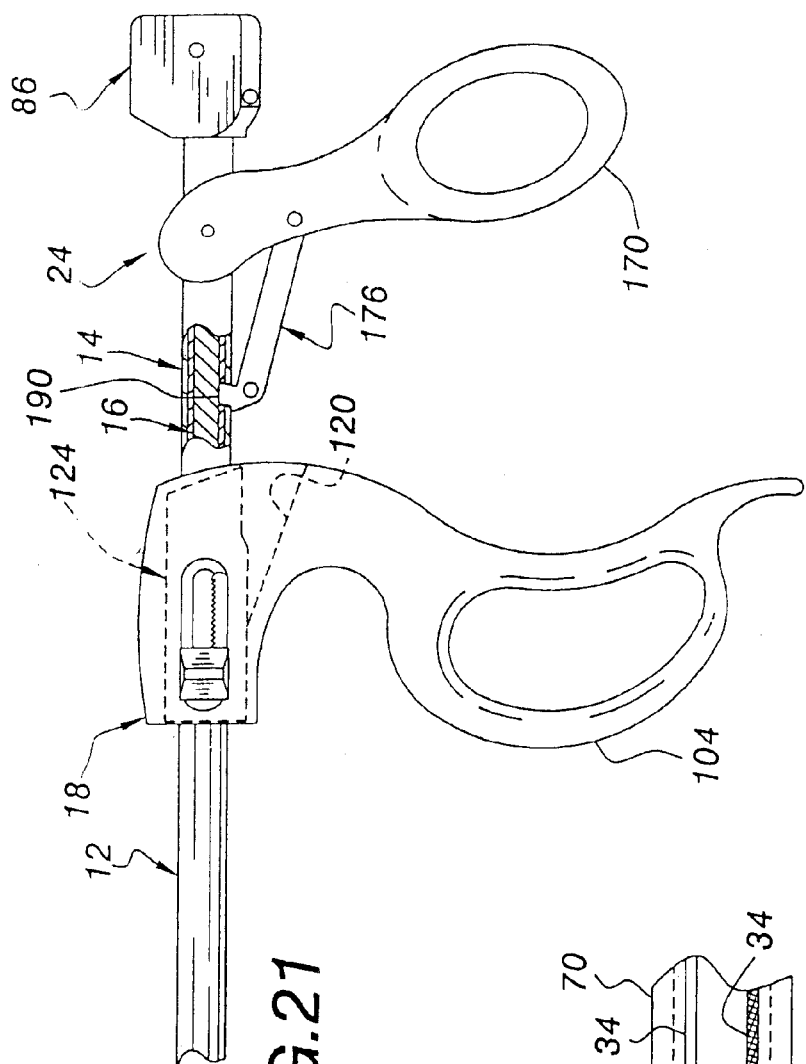
FIG.21
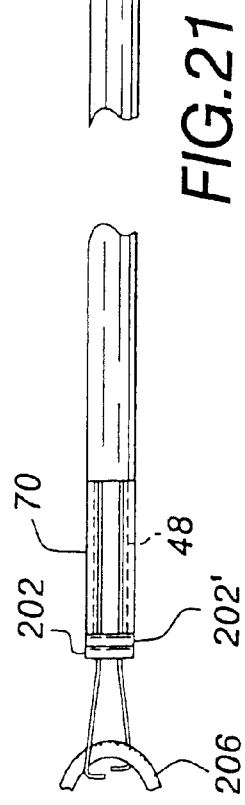
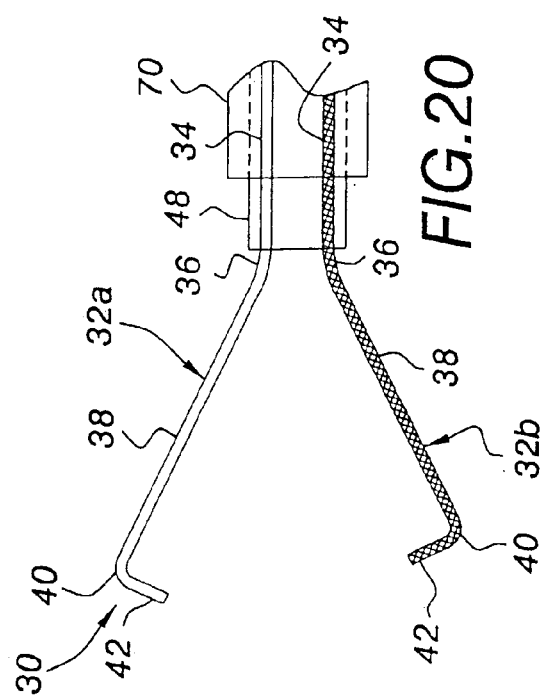
FIG.20

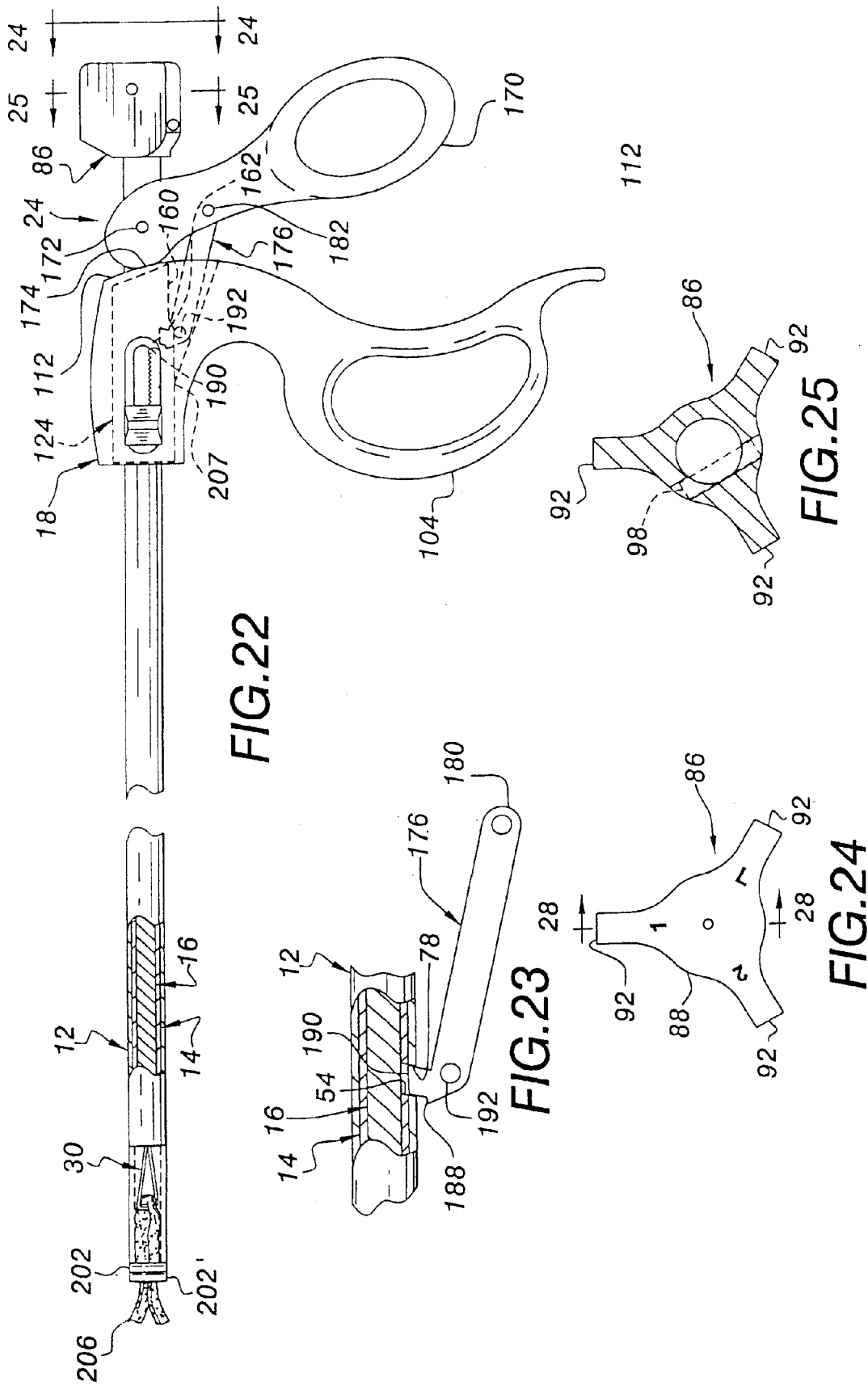

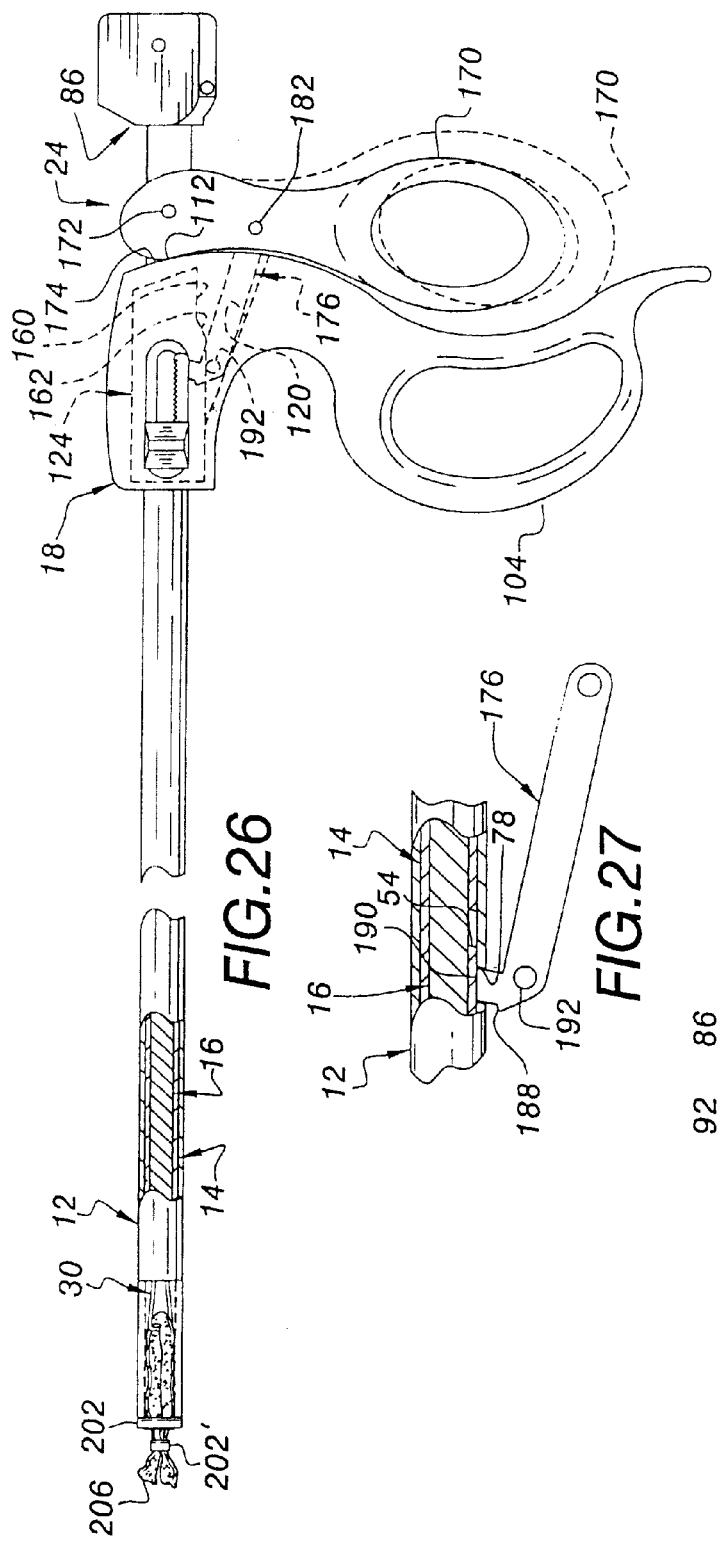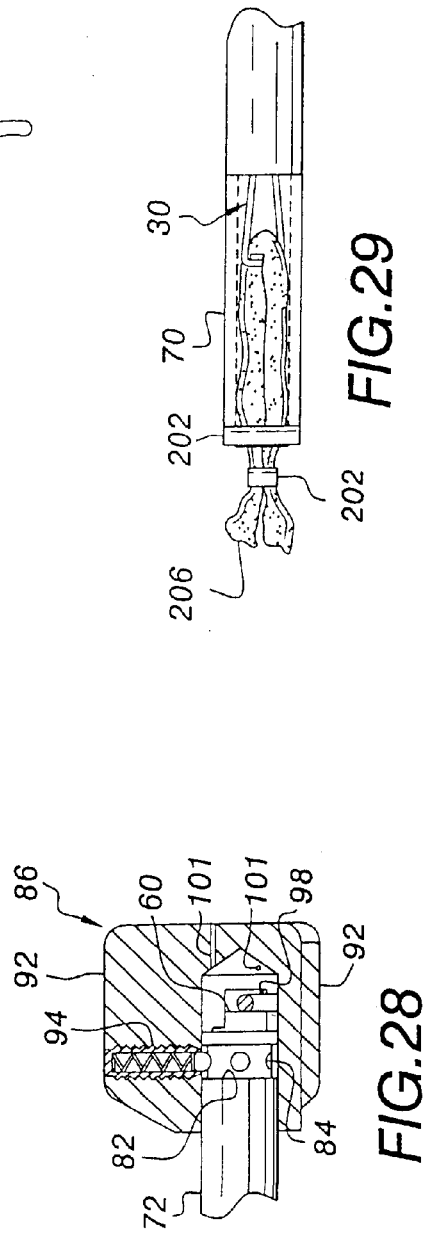

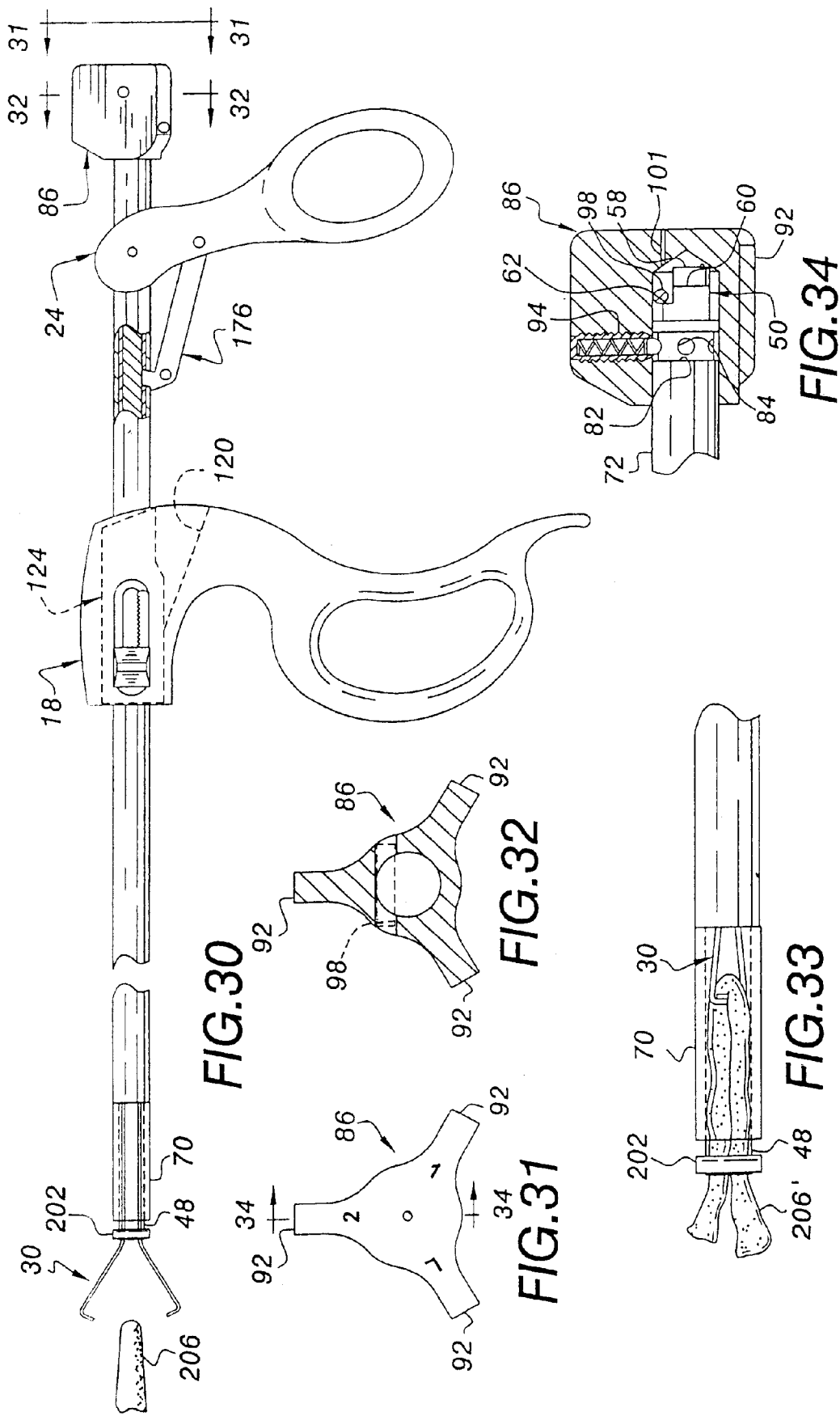

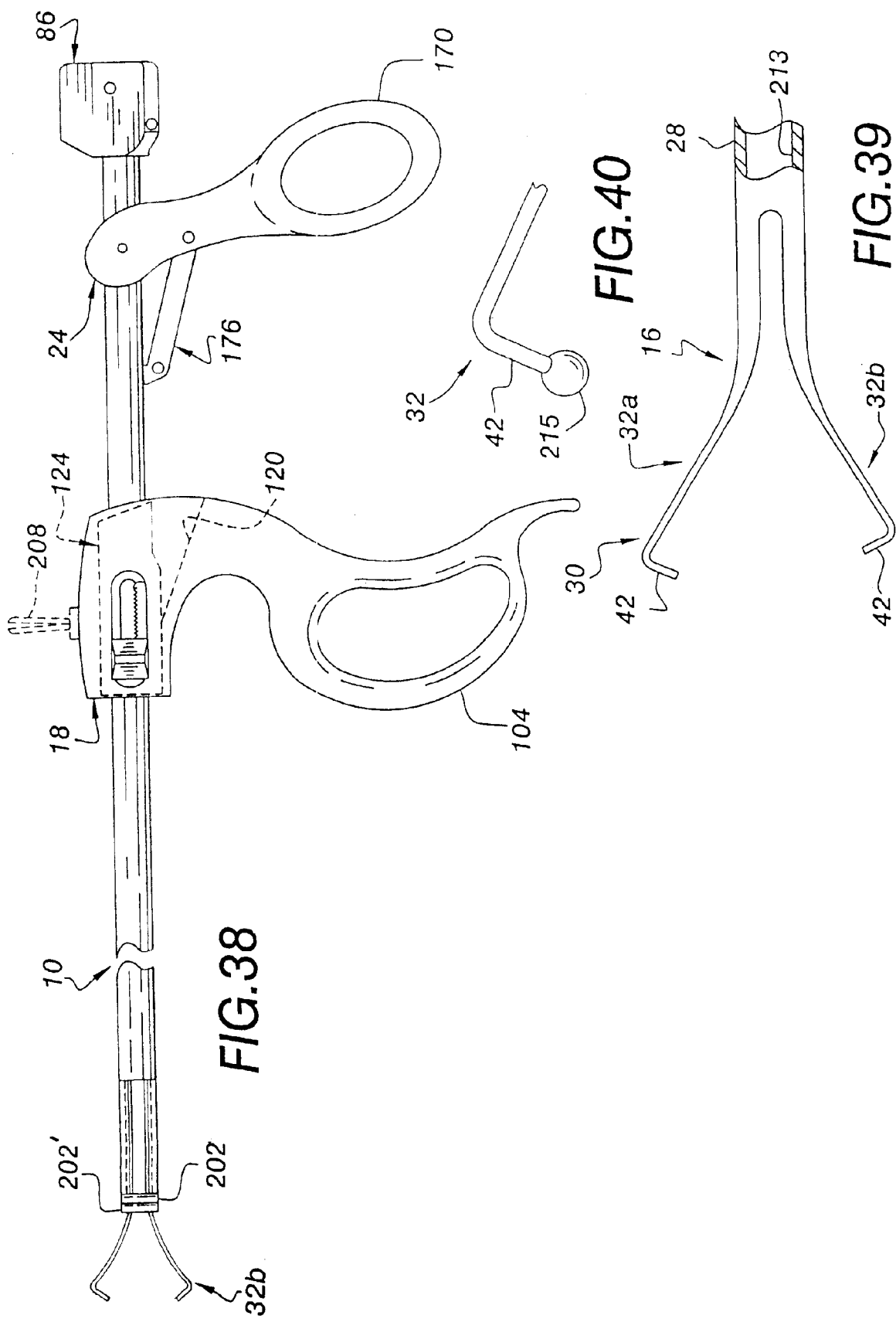

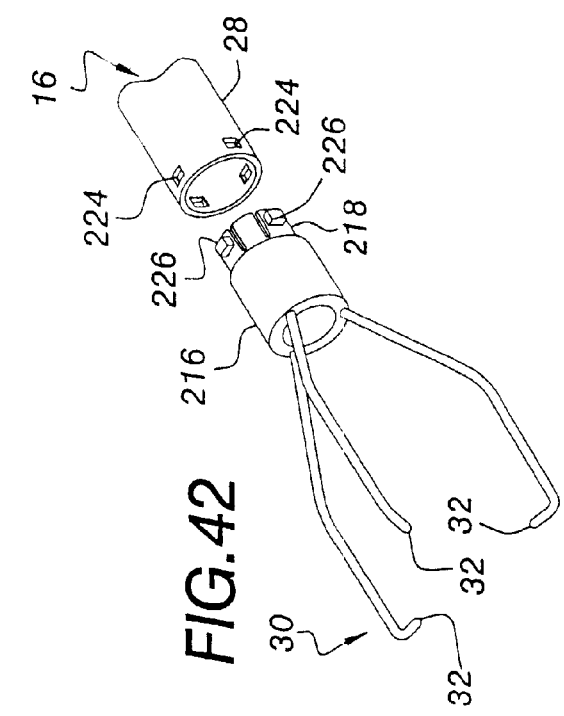
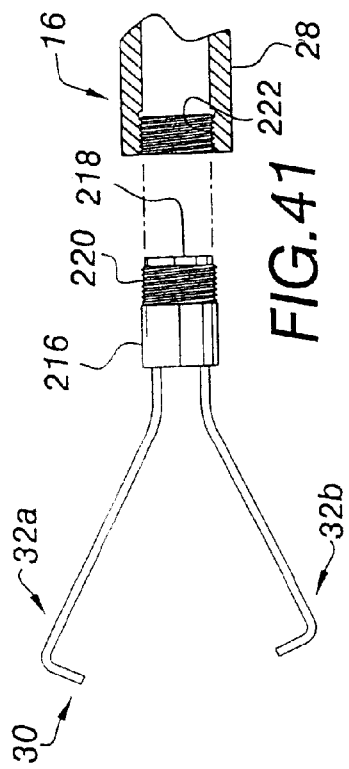
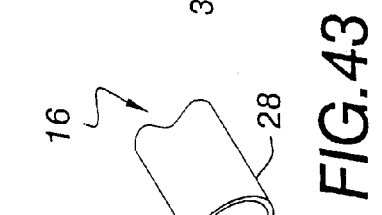
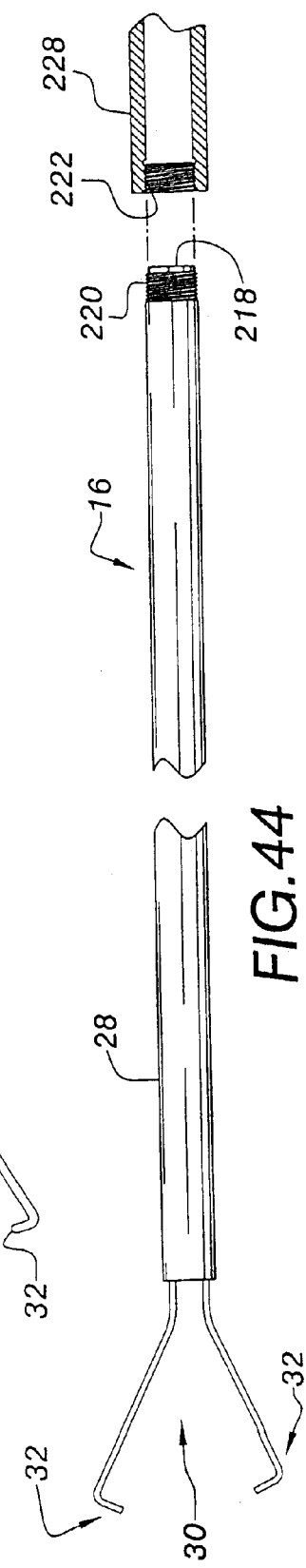

RING APPLICATOR AND METHOD FOR APPLYING ELASTIC RINGS TO ANATOMICAL TISSUE STRUCTURES

BACKGROUND OF THE INVENTION

1. Field of the Invention

The present invention relates generally to surgical devices and, more particularly, to a ring applicator and method for applying one or more elastic rings to anatomical tissue structures such as the fallopian tubes.

2. Discussion of the Background Art

A variety of procedures have been developed to accomplish female sterilization by obstructing the fallopian tubes in order to prevent fertilization of the ova. The traditional procedure involves tying off each tube with ligatures and then cutting between the ligatures to permanently remove a section of the tubing. Another type of procedure utilizes electrocautery instruments to burn through and permanently seal each of the fallopian tubes. These procedures involve significant discomfort for the patient, and highly skilled personnel are required to complete the operation successfully. With respect to cauterization, in particular, there is the possibility of inadvertently burning other organs of the body and, for example, accidentally perforating the bowel.

The foregoing procedures are also undesirable in that they effect a sterilization which is permanent and cannot easily be reversed. In theory, plastic or metal clips can be applied to each tube in order to effect a sterilization which can be reversed; however, in practice, the clips have sometimes fallen off, thereby rendering the sterilization ineffective. Another type of reversible procedure which has gained wide acceptance in many parts of the world involves drawing the fallopian tube into a loop or knuckle within a tubular member carrying an elastic ring and slipping the elastic ring onto the loop in order to obstruct or ligate the tube. Typically, a forceps is used to draw the fallopian tube into a loop within a first tubular member. The first tubular member containing the loop is then caused to move axially relative to a second tubular member disposed telescopically around the first tubular member such that an elastic ring is forced off the distal end of the first tubular member onto the midsection of the loop, thereby occluding the fallopian tube.

A number of ring applicators have been developed to ligate tubular organs such as the fallopian tube. A first type of ring applicator, exemplified by U.S. Pat. Nos. 3,911,923 and 4,374,523 to Yoon, and U.S. Pat. Nos. 4,257,420 and 4,471,766 to Terayama, is designed to ligate only one fallopian tube at a time. Thus, in such devices, after one of the fallopian tubes has been occluded by placing an elastic ring around a loop formed in the fallopian tube, it is necessary to completely withdraw the instrument from the patient and reload the instrument with another elastic ring to ligate the second fallopian tube. Such a technique is not only time consuming, but also unduly complicates the tubal ligation procedure and, in some instances, can increase the chance of infection.

Another type of ring applicator, exemplified by U.S. Pat. No. 4,230,116 to Watson and U.S. Pat. No. 4,548,201 to Yoon, permits multiple rings to be carried at the distal end of a first tubular member disposed telescopically within a second tubular member, but relies on user skill to eject the rings individually by retracting the first tubular member partially to eject the first ring and fully to eject the second ring. A disadvantage of this type of ring applicator is that it is difficult to determine when the first ring has been ejected to know when to stop retracting the first tubular member. It is therefore possible for inexperienced or unskilled operators to eject both rings onto the first fallopian tube thereby requiring withdrawal of the instrument from the operative site for reloading before the second fallopian tube can be ligated.

Yet another type of ring applicator, exemplified by U.S. Pat. Nos. 4,226,239 and 4,493,319 to Polk, et al., utilizes an adjustable stop to limit displacement of the first tubular member relative to the second tubular member to an appropriate amount for each ring. In these devices, movement of the first and second tubular members is linked to handles, with the stop being positionable between the handles to prevent full retraction of the first tubular member in the case of the first ring and being removable from between the handles to permit full retraction of the first tubular member for ejecting the second ring. U.S. Pat. No. 4,493,319 also discloses a locking mechanism for preventing relative movement between the first and second tubular members to facilitate loading of elastic rings. However, the locking mechanism operates independently of the adjustable stop and does not allow the forceps to be fully deployed when in use.

A disadvantage of prior art ring applicators in general is that ejection of the rings occurs automatically with retraction of the forward or distal handle thereby limiting the ability of the surgeon to control the order and timing of the steps involved in the procedure. Another disadvantage of prior art ring applicators is that these devices do not permit rings to be ejected until the anatomical tissue structure has been drawn into the first tubular member a predetermined distance which is fixed. Depending on the type of anatomical tissue structure being ligated and other operating conditions, it may be desirable to retract greater or shorter lengths of tissue prior to ejecting a ring. Still another disadvantage of prior art ring applicators is that it is typically not possible to observe the anatomical tissue once it has been retracted into the tubular member in order to determine whether the tissue is properly positioned prior to ejecting an elastic ring.

SUMMARY OF THE INVENTION

Accordingly, it is a primary object of the present invention to overcome the abovementioned disadvantages of the prior art and to improve ring applicators having adjustable stops which limit axial movement of telescoping members to permit multiple elastic rings to be applied to anatomical tissue structures in a reliable manner.

It is another object of the present invention to simplify operation of a ring applicator having an adjustable stop and a locking mechanism for preventing relative axial movement of the telescoping members during ring loading by incorporating a locking mechanism into the adjustable stop.

It is yet another object of the present invention to permit independent tissue retraction and ring ejection operations to be performed with a ring applicator by coupling a forceps with a first handle and telescoping members with a second handle axially movable relative to the first handle and pivotably movable relative to the telescoping members.

It is an additional object of the present invention to assure proper placement of anatomical tissue structures within tubular members of a ring applicator prior to ejecting a ring by providing the tubular members with transparent tips having scale markings for comparison with the tissue structures.

Yet another object of the present invention is to enable surgeons to determine the relative lengths of grasping members used to draw anatomical tissue structures into a tubular member of a ring applicator in order to prevent improper use of the grasping members which may cause damage to the anatomical tissue structures.

The present invention has another object in permitting an elastic ring to be ejected onto an anatomical tissue structure which has not been fully drawn into a first tubular member of a ring applicator so that, for example, the ring applicator can be used to ligate anatomical tissue structures of various sizes.

The aforesaid objects can be achieved individually or in combination, and it is not intended that the present invention be construed as requiring two or more of the objects to be achieved in combination unless expressly required by the attached claims.

The present invention is generally characterized in a ring applicator for applying elastic rings to anatomical tissue during surgical procedures including an inner member with a forceps movably disposed within a middle tubular member having a distal portion configured to hold an elastic ring in an expanded state and a proximal portion with a plurality of longitudinally spaced abutment surfaces or steps. The middle tubular member is movably disposed in an outer tubular member, and an adjustable stop mechanism is mounted on the proximal end of the outer tubular member to limit axial movement of the outer tubular member relative to the middle tubular member by aligning a stop member with a different abutment surface in each stop position. A distal handle is preferably connected with the inner member via slots in the outer and middle tubular members, and a proximal handle is preferably pivotally connected to the middle tubular member via a slot in the outer tubular member. In a preferred embodiment, a pusher has a proximal end pivotally connected with the proximal handle and a distal end movable between a latched position where the distal end of the pusher protrudes into apertures in the outer and middle tubular members to prevent pivotal movement of the proximal handle and an unlatched position where the distal end of the pusher is disengaged from the aperture in the middle tubular member to permit pivotal movement of the proximal handle in order to move the outer tubular member axially relative to the middle tubular member to eject an elastic ring.

Another aspect of the present invention is generally characterized in a ring applicator for applying elastic rings to anatomical tissue during a surgical procedure including an outer tubular member having an aperture formed therein, a middle tubular member movably disposed within the outer tubular member and having an aperture formed therein, and an elongate inner member movably disposed within the middle tubular member and having a forceps at a distal end. A distal handle is connected to the inner member via slots in the outer and middle tubular members, and a proximal handle is pivotally connected to the middle tubular member via a slot in the outer tubular member. The proximal handle carries a pusher having a proximal end pivotally connected with the proximal handle and a distal end movable between a latched position where the distal end of the pusher protrudes into the apertures to prevent pivotal movement of the proximal handle and relative axial movement between the outer and middle tubular members, and an unlatched position where the distal end of the pusher is disengaged from the aperture in the middle tubular member to permit pivotal movement of the proximal handle in order to move the outer tubular member axially relative to the middle tubular member to eject a ring. In a preferred embodiment, the pusher includes a cam follower, such as a peg, which slides along a cam surface in the distal handle when the handles are moved toward one another, thereby causing the pusher to become disengaged from the middle tubular member. The cam surface can, for example, be defined by a knuckle slide movably disposed in the distal handle. Moving the knuckle slide relative to the distal handle allows a ring to be ejected when the handles are axially spaced from one another so that, for example, anatomical tissue structures of various sizes can be ligated. When provided, the knuckle slide can include a ratcheting feature which is released in response to engagement of the pusher with the knuckle slide.

Yet another aspect of the present invention is generally characterized in a ring applicator for applying elastic rings to anatomical tissue in surgical procedures including an outer tubular member, a middle tubular member movably disposed within the outer tubular member and having a distal portion configured to receive an elastic ring in an expanded condition, and an elongate inner member movably disposed within the middle tubular member and including a pair of opposed grasping members at a distal end, the grasping members having pivot arms of unequal length with distal tips oriented transverse to the arms such that one of the tips is disposed proximally of the other tip when the grasping members are in a closed condition, wherein at least a portion of one of the grasping members has a color allowing the one grasping member to be visually distinguished from the other grasping member when the grasping members are viewed remotely via an endoscope.

An additional aspect of the present invention is generally characterized in a ring applicator for applying elastic rings to anatomical tissue in surgical procedures including an outer tubular member, a middle tubular member movably disposed within the outer tubular member and having a distal portion configured to receive an elastic ring in an expanded condition, and an elongate inner member movably disposed within the middle tubular member and including a forceps at a distal end for grasping anatomical tissue and drawing the tissue into the middle tubular member, wherein the outer tubular member and the middle tubular member includes a transparent distal portion with scale markings for measuring anatomical tissue drawn into the middle tubular member.

Still another aspect of the present invention is generally characterized in a method of applying elastic rings to anatomical tissue during surgical procedures using a ring applicator having a middle tubular member disposed within an outer tubular member, and an inner member with forceps disposed within the middle tubular member, the method including the steps of positioning the middle tubular member to protrude distally from the outer tubular member, adjusting a stop mechanism on the proximal end of the outer tubular member to engage a first of a plurality of longitudinally spaced abutment surfaces or steps at a proximal end of the middle tubular member such that the middle tubular member is prevented from moving axially relative to the outer tubular member, loading elastic rings onto the distal end of the middle tubular member, inserting the ring applicator into the body, grasping a first anatomical tissue structure using the forceps, pulling the tissue into the middle tubular member, adjusting the stop mechanism on the proximal end of the outer tubular member to position the stop member proximally of a second abutment surface along the proximal portion of the middle tubular member such that the outer tubular member can move axially about one ring width relative to the middle tubular member to eject a first ring from the distal end of the middle tubular member onto the tissue, and releasing the first anatomical tissue structure from the middle tubular member. A plurality of elastic rings can be loaded onto the distal portion of the middle tubular member during the loading step and, in a preferred embodiment, the method further includes the steps of grasping a second anatomical tissue structure using the forceps, drawing the second anatomical tissue structure into the middle tubular member, adjusting the stop mechanism on the proximal end of the outer tubular member to position the stop member proximally of a third abutment surface along the proximal portion of the middle tubular member such that the outer tubular member can move axially about two ring widths relative to the middle tubular members, ejecting a second elastic ring from the distal end of the middle tubular member onto the second anatomical tissue structure by moving the outer tubular member distally relative to the middle tubular member until the stop member contacts the third abutment surface, and releasing the second anatomical tissue structure from the middle tubular member.

Yet another aspect of the present invention is generally characterized in a method of applying elastic rings to anatomical tissue during surgical procedures using a ring applicator having a middle tubular member disposed within an outer tubular member, an elastic ring mounted on a distal portion of the middle tubular member, and an inner member with a forceps disposed within the middle tubular member, the forceps having opposed grasping members of unequal length and of different color, the method including the steps of inserting a distal end of the ring applicator into a body cavity, spreading the grasping members of the forceps apart, observing the color of the grasping members to determine which grasping member is shorter, positioning the anatomical tissue proximally of the tip of the shorter grasping member, grasping the anatomical tissue using the forceps, pulling the anatomical tissue into the middle tubular member using the forceps, and ejecting a ring from the middle tubular member onto the anatomical tissue by moving the outer tubular member distally relative to the middle tubular member.

Still another aspect of the present invention is generally characterized in a method of applying elastic rings to anatomical tissue during surgical procedures using a ring applicator having a middle tubular member with a transparent tip disposed within an outer tubular member with a transparent tip, and an inner member with a forceps disposed within the middle tubular member, the method including the steps of inserting the ring applicator into a body cavity, grasping anatomical tissue using the forceps, pulling the anatomical tissue into the middle tubular member using the forceps, viewing the anatomical tissue through the transparent tips of the outer and middle tubular members, measuring the length of the anatomical tissue against scale markings on one or both of the transparent tips, and ejecting a ring from the middle tubular member onto the anatomical tissue by moving the outer tubular member distally relative to the middle tubular member.

A further aspect of the present invention is generally characterized in a method of applying elastic rings to anatomical tissue structures during surgical procedures using a ring applicator having a middle tubular member disposed within an outer tubular member and connected to a proximal handle, and an inner member with forceps disposed within the middle tubular member and connected to a distal handle. The method includes the steps of positioning the middle tubular member in a loading position where a distal end of the middle tubular member protrudes distally from the outer tubular member, locking the middle tubular member in the loading position, moving the forceps to a retracted position within the middle tubular member by sliding the proximal and distal handles together such that the handles abut one another, loading an elastic ring onto a distal portion of the middle tubular member, inserting the ring applicator into the body, moving the forceps to an extended position protruding from the middle tubular member by sliding the proximal and distal handles apart such that the handles are axially spaced from one another, positioning the forceps around a first anatomical structure, pulling the first anatomical tissue structure into the middle tubular member with the forceps by sliding the proximal and distal handles together such that the handles abut one another, unlocking the middle tubular member so that the outer and middle tubular members can move axially relative to one another, and ejecting the elastic ring onto the first anatomical structure by pivoting the proximal handle about the point of contact between the handles to cause the outer tubular member to move distally relative to the middle tubular member.

Another aspect of the present invention is generally characterized in a method of applying elastic rings to anatomical tissue structures during surgical procedures using a ring applicator having a middle tubular member disposed within an outer tubular and connected to a proximal handle, and an inner member with forceps disposed within the middle tubular member and connected to a distal handle. The method includes the steps of positioning the middle tubular member in a loading position where a distal end of the middle tubular member protrudes distally from the outer tubular member, locking the middle tubular member in the loading position, moving the forceps to a retracted position within the middle tubular member by sliding the proximal and distal handles together such that the handles abut one another, loading an elastic ring onto a distal portion of the middle tubular member, inserting the ring applicator into the body, moving the forceps to an extended position protruding from the middle tubular member by sliding the proximal and distal handles apart such that the handles are axially spaced from one another, positioning the forceps around a first anatomical structure, pulling the first anatomical tissue structure into the middle tubular member with the forceps by sliding the proximal and distal handles together such that the handles are axially spaced apart, moving a knuckle slide disposed within the distal handle proximally relative to the distal handle such that a proximal surface of the knuckle slide abuts the proximal handle, unlocking the middle tubular member so that the outer and middle tubular members can move axially relative to one another, ejecting the elastic ring onto the first anatomical structure by pivoting the proximal handle about the point of contact between the proximal handle and the knuckle slide to cause the outer tubular member to move distally relative to the middle tubular member.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 1 is a side view, broken longitudinally, of a ring applicator according to the present invention.

FIG. 3 is a fragmentary perspective view of the proximal end of a middle tubular member for use with a ring applicator according to the present invention.

FIG. 4 is a rear view of the middle tubular member shown in FIG. 3.

FIG. 5 is a rear view of a stop adjustment knob for a ring applicator according to the present invention taken along line 5—5 in FIG. 1.

FIG. 6 is a cross-sectional view of a stop adjustment knob for a ring applicator according to the present invention taken along line 6—6 in FIG. 1.

FIG. 7 is a side view, partly in section, of a stop adjustment knob for a ring applicator according to the present invention taken along Line 7—7 in FIG. 5.

FIG. 8 is a fragmentary rear view of a distal handle for a ring applicator according to the present invention.

FIG. 9 is a fragmentary sectional view of a distal handle for a ring applicator according to the present invention taken through line 9—9 in FIG. 8.

FIG. 10 is bottom plan view of a knuckle slide for a ring applicator according to the present invention.

FIG. 11 is a side view in elevation of the knuckle slide shown in FIG. 10.

FIG. 12 is a rear view of the knuckle slide taken along line 12—12 in FIG. 11.

FIG. 13 is a sectional view of the knuckle slide taken along line 13—13 in FIG. 11.

FIG. 14 is a sectional view of the knuckle slide taken along line 14—14 in FIG. 11.

FIG. 15 is a side view, broken longitudinally, of a ring applicator according to the present invention with forceps in an open position.

FIG. 16 is an enlarged fragmentary side view of the distal end of a pusher protruding through openings formed in outer and middle tubular members of a ring applicator according to the present invention.

FIGS. 17–19 are fragmentary side views of the distal end of a ring applicator according to the present invention illustrating a method of loading elastic rings.

FIG. 20 is a fragmentary side view of the distal end of a modification of a ring applicator according to the present invention wherein the forceps is color coded.

FIG. 21 is a side view, broken longitudinally, of a ring applicator according to the present invention illustrating use of the forceps to draw a fallopian tube into the middle tubular member.

FIG. 22 is a side view, broken longitudinally, of a ring applicator according to the present invention with the forceps fully retracted and the stop adjustment knob positioned to select the first elastic ring.

FIG. 23 is an enlarged fragmentary side view, partly in section, illustrating the distal end of the pusher disengaged from the middle tubular member.

FIG. 24 is a rear view of the stop adjustment knob taken along line 24—24 in FIG. 22.

FIG. 25 is a sectional view of the stop adjustment knob taken along line 25—25 in FIG. 22.

FIG. 26 is a side view, broken longitudinally, of a ring applicator according to the present invention after a first ring has been ejected from the middle tubular member.

FIG. 27 is an enlarged fragmentary side view, partly in section, illustrating the distal end of the pusher moved axially relative to the opening in the middle tubular member.

FIG. 28 is a sectional side view of the stop adjustment knob taken along line 28—28 in FIG. 24.

FIG. 29 is an enlarged fragmentary side view of the distal end of the ring applicator shown in FIG. 26.

FIG. 30 is a side view, broken longitudinally, of a ring applicator according to the present invention ready to grasp the second fallopian tube in a female sterilization procedure.

FIG. 31 is a rear view of the stop adjustment knob taken along line 31—31 in FIG. 30.

FIG. 32 is a sectional view of the stop adjustment knob taken along line 32—32 in FIG. 30.

FIG. 33 is a fragmentary side view of the distal end of a ring applicator according to the present invention after the second fallopian tube has been retracted into the middle tubular member in a female sterilization procedure.

FIG. 34 is a sectional view of the stop adjustment knob taken along line 34—34 in FIG. 31.

FIG. 38 is a side view, broken longitudinally, of a modification of a ring applicator according to the present invention.

FIG. 39 is a fragmentary side view of the distal end of a modified inner member for the ring applicator according to the present invention.

FIG. 40 is a fragmentary side view of a modified tip for a grasping member of the ring applicator according to the present invention.

FIG. 41 is an exploded fragmentary side view of a detachable forceps for use with the ring applicator according to the present invention.

FIG. 42 is an exploded fragmentary perspective view of another detachable forceps for use with the ring applicator according to the present invention.

FIG. 43 is an exploded fragmentary perspective view of yet another detachable forceps for use with the ring applicator according to the present invention.

FIG. 44 is a side view, broken longitudinally, of a detachable inner member for with the ring applicator according to the present invention.

DESCRIPTION OF THE PREFERRED EMBODIMENTS

Figure 2:
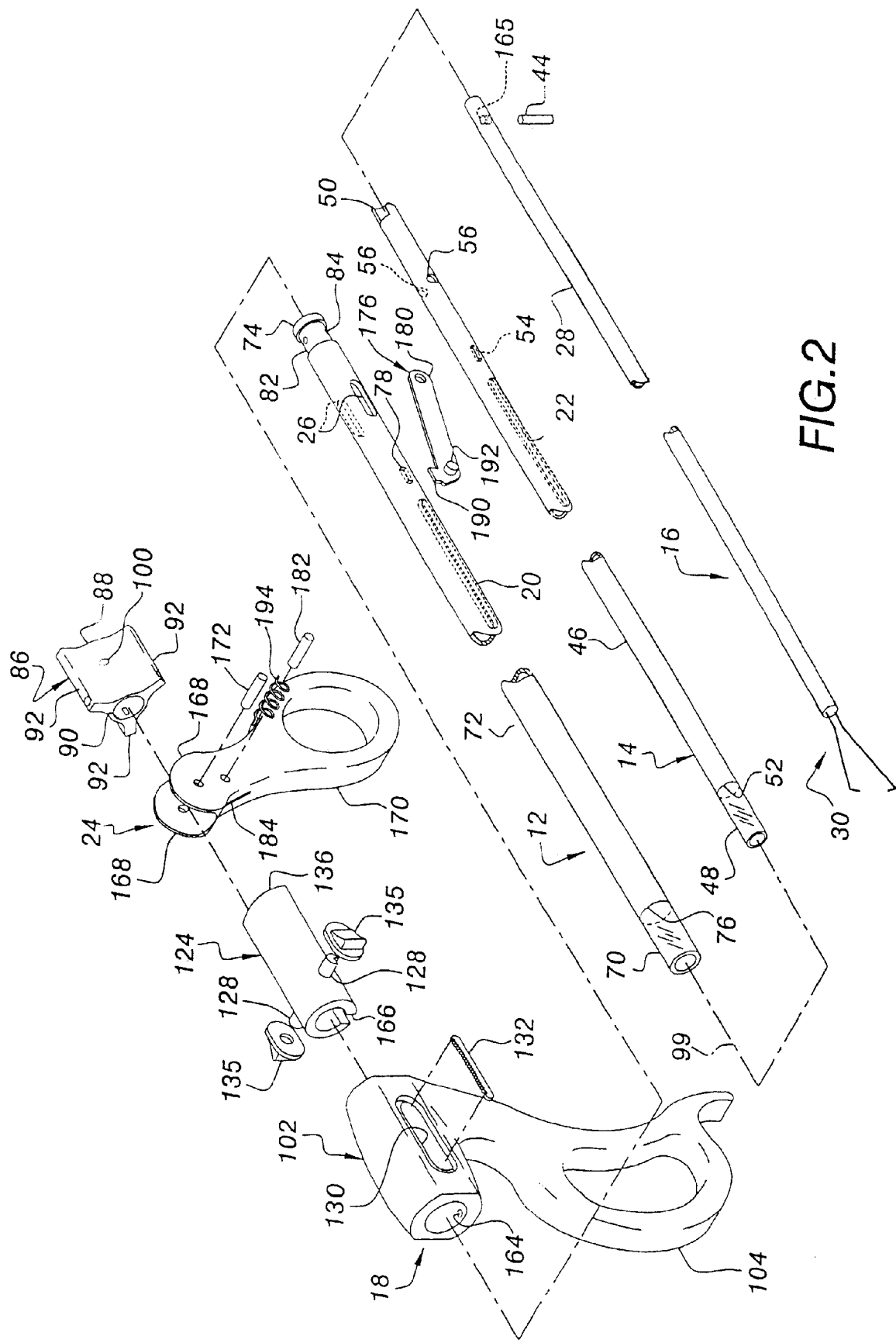
FIG. 2 is an exploded perspective view of the ring applicator shown in FIG. 1.

A ring applicator 10 according to the present invention, as illustrated in FIGS. 1 and 2, includes an outer tubular member 12, an intermediate or middle tubular member 14 telescopically received within the outer tubular member, and an elongate inner member 16 telescopically received within the middle tubular member. Inner member 16 is connected to a forward, distal or first handle 18 via slots 20 and 22 in outer and middle tubular members 12 and 14, respectively. A rearward, proximal or second handle 24 is disposed proximally of first handle 18 and is pivotally connected to middle tubular member 14 via slots 26 on opposite sides of outer tubular member 12.

As best seen in FIG. 2, inner member 16 is made up of an elongate rod 28 with a forceps 30 at a distal end of the rod. Forceps 30 includes a pair of laterally opposed grasping members or graspers 32a and 32b formed of a length of wire made of stainless steel or any other medical grade material having sufficient elasticity to return to a normally open position as shown in FIG. 2 after having been held in a closed position within the middle tubular member as shown in FIG. 1. Grasping members 32a and 32b each include a straight portion 34 extending from the distal end of rod 28 to a first bend 36 connecting the straight portion with an angled portion 38. Angled portion 38 extends laterally outward at an acute angle relative to the distal direction from the first bend to a second bend 40 connecting the angled portion with a distal tip 42 extending perpendicularly inward from the second bend. Looking at FIGS. 1 and 2, it can be seen that the bottom grasping member 32b is slightly shorter than the top grasping member 32a so that, when the forceps are in the closed configuration shown in FIG. 1, the tip of the bottom grasping member will be disposed proximally of the tip of the top grasping member in an overlapping or longitudinally offset manner. As will be explained in greater detail below, the shorter grasping member is used to snag the fallopian tube and the longer grasping member is used to trap the fallopian tube. In a preferred embodiment, the grasping members are about two inches long and formed of 0.040 inch diameter stainless steel wire. The top grasping member is preferably at least about 0.040 inch longer than the bottom grasping member, with a tip length of about 0.160 inch compared with a tip length of about 0.120 inch for the bottom grasping member. In the open or extended position shown in FIG. 2 the grasping members protrude about one inch from the distal end of middle tubular member with about a 0.40 inch gap between the grasping members. In the closed or retracted position shown in FIG. 1 the grasping members are preferably proximally spaced about 0.560 inch from the distal end of the middle tubular member. Rod 28 is shown as a solid cylinder and can be made of any material sufficiently rigid to slide within the middle tubular member including, but not limited to, plastic and metal materials. The rod terminates proximally at first handle 18 and is configured to receive a pin 44 adjacent the proximal end of the rod.

Middle tubular member 14 includes an elongate tubular body 46 and a transparent tip 48 on the distal end of the tubular body. Tubular body 46 is shown as a hollow tubular member of circular cross-section but can have any cross-sectional configuration to slide within outer tubular member 12 and can be made of any suitable material including, but not limited to, metals such as stainless steel and plastics. Referring to FIG. 2, longitudinal slot 22 is formed in middle tubular member 14 between proximal and distal ends 50 and 52 of tubular body 46. The length of slot 22 is such that when the inner member 16 is connected to first handle 18 by a pin extending through the slot, the inner member can be moved a sufficient distance relative to the middle tubular member in order to cause forceps 30 to open and close. A small rectangular opening or aperture 54 is formed in the tubular body proximally of longitudinal slot 22 for reasons that will be explained below. A pair of handle mounting holes 56 are also formed at diametrically opposed locations near the proximal end of the tubular body about 0.90 inches from the longitudinal slot and aperture. As best seen in FIGS. 2–4, the proximal end of the tubular body 46 is notched to define longitudinally spaced abutment surfaces or steps 58, 60 and 62 about the circumference of the tubular body, each step having a circumferential length of about 120°. Referring to FIGS. 3 and 4 in particular, it can be seen that the first step 58 extends clockwise from a first longitudinal notch edge 64 to a second longitudinal notch edge 66 shorter than the first notch edge. The second longitudinal notch edge 66 extends distally from first step 58 to second step 60 which extends clockwise, looking at FIGS. 3 and 4, from the second longitudinal notch edge to a third longitudinal notch edge 68 extending distally from the second step to third step 62. The third step 62 extends clockwise, looking at FIGS. 3 and 4, from third longitudinal notch edge 68 to first longitudinal notch edge 64. The longitudinal spacing between the first and second steps and between the second and third steps is approximately equal to the thickness or width of an individual elastic ring (e.g., about 0.065 inch).

Referring again to FIGS. 1 and 2, it can be seen that transparent tip 48 is a hollow tubular member of cylindrical configuration formed of a transparent material such as, for example, acrylic plexiglass. Transparent tip 48 has an outer diameter configured to hold elastic rings in an expanded state and an inner diameter configured to receive an anatomical tissue structure, such as a knuckled or looped fallopian tube. A distal end 69 of the transparent tip preferably has a full radius finish, i.e., both outside and inside edges are rounded off, to prevent damage to the anatomical tissue structure as it is drawn into the middle tubular member and to prevent damage to the rings when loading them onto the ring applicator. For female sterilization, the inner diameter is preferably about 0.176 inch and the outer diameter is preferably about 0.212 inch. The transparent tip has a length (e.g., about 1.25 inches) such that at least tips of the forceps members 32a and 32b can be seen from outside the ring applicator instrument when inner member 16 is in its proximal most position relative to middle tubular member 14 regardless of the position of the middle tubular member relative to outer tubular member 12. The transparent tip can be attached to the tubular body by use of adhesives, friction-fit, threaded engagement, tubular couplings, or any other suitable method.

Referring still to FIGS. 1 and 2, outer tubular member 12 includes a transparent tip 70 mounted at the distal end of an elongate tubular body 72, the tubular body and tip both being of hollow cylindrical configuration with an inner diameter (e.g., about 0.230 inch) to receive the middle tubular member therein in telescoping relation and an outer diameter (e.g., about 0.310 inches) to fit through a portal. The transparent tip 70 can be formed of any transparent material, such as acrylic plexiglass, can be attached to the tubular body in any of the ways described above, and can be shorter, longer or about the same length as the transparent tip or tube 48 at the distal end of middle tubular member 14 so long as the transparent portions overlap to provide a complete view of anatomical tissue structures drawn into the middle tubular member using the forceps. Preferably, the transparent tip 70 at the distal end of outer tubular member 12 is slightly shorter than the middle tubular member tip 48 (e.g., about 1.0 inch long). A distal end 73 of transparent tip 70 can have a flat, radiused, or chamfered finish but is preferably provided with a full radius finish along an outer edge, a small (e.g., 0.020 inch) chamfer along an inner edge, and a flat between the radiused and chamfered edges.

Longitudinal slot 20 is formed in outer tubular member 12 between proximal and distal ends 74 and 76 of the tubular body. A small rectangular opening or aperture 78 is formed in tubular body 72 proximally of slot 20, and both the slot and the aperture are aligned with the corresponding slot and aperture in the middle tubular member when the distal end 69 of the middle tubular member protrudes a predetermined distance (e.g., between about 0.215 inch and about 0.239 inch) from the distal end 73 of the outer tubular member, the predetermined distance preferably corresponding substantially to the thickness or width of a pair of elastic rings. A pair of diametrically opposed handle mounting slots 26 are formed in tubular body 72 between the rectangular aperture and the proximal end of the tubular body about 90° from the longitudinal slot and the aperture. In addition, as best seen in FIG. 2, an annular groove 82 with circumferentially spaced recesses 84 of generally hemispherical configuration is formed in tubular body 72 adjacent proximal end 74 of the tubular body.

An adjustable stop is shown in FIGS. 5–7 as a knob 86 having a generally cylindrical body 88 defining a cylindrical recess or bore 90 for receiving the proximal end of outer tubular member 12 and three fins 92 of plate-like configuration extending radially outward from the body of the knob at equiangularly spaced locations. Spring-loaded ball detents 94 are inserted into holes formed radially through the fins and the body of knob 86 to engage the recesses 84 formed in the annular groove 82 at the proximal end of outer tubular member 12 so the knob can be selectively rotated into one of three predetermined positions as indicated by markings (e.g., "L" for loading or locked, "1" for first ring, and "2" for second ring) on the proximal face 96 of the knob. A pin 98 extends across the cylindrical bore of knob 86 in a plane perpendicular to the longitudinal axis 99 of the outer tubular member to function as a stop member which engages the notched proximal end 50 of the middle tubular member to limit axial displacement relative to the outer tubular member. Opposite axial ends of the stop member or pin 98 are anchored in holes 100 formed in the knob body on opposite sides of the fin labeled "2" so that the stop member is laterally offset from the central longitudinal axis 99 of the bore to traverse the cross-section across a chord (e.g., by transacting an arc of about 120°). Proximal face 96 of the knob is a flat, planar surface oriented substantially perpendicular to a longitudinal axis 99, and a port 101 is shown extending through the proximal face of the knob to provide access to the operative site from outside the body. One or more operating channels (not shown) can extend through the inner, outer and middle members.

The first or distal handle 18 includes a generally cylindrical housing 102 and a finger loop 104 extending downwardly from a proximal end of the handle housing. Handle housing 102 includes spaced parallel side walls 106, a generally flat distal surface or face 108 oriented perpendicular to the side walls, a top surface or face 110, and a beveled proximal surface or face 112 extending proximally in the downward direction from the top surface. A bottom surface or face 114 of the handle housing extends rearwardly from the distal surface or face of the housing and curves downwardly to connect with a concave surface 116 between the housing and finger loop 104. Referring to FIGS. 8 and 9, in particular, a cylindrical bore or channel 118 is formed longitudinally through handle housing 102 to receive a knuckle slide 124 in a telescoping manner. A narrow slot or groove 120 extends downwardly from cylindrical channel 118, looking at FIGS. 8 and 9, and is of increasing depth in the direction of proximal housing surface 112 to define a generally triangular cavity communicating between the cylindrical channel and the proximal face of the handle housing. A second slot or groove 122 of generally rectangular configuration and greater width than slot 120 extends downwardly from the cylindrical channel, looking at FIGS. 8 and 9, along an upper edge of slot 120 to define a shoulder or track along laterally opposed sides of the triangular cavity.

Knuckle slide 124 is movably disposed within the longitudinal channel defined through handle housing 102 and can be formed of any suitable material including, but not limited to, metals such as stainless steel and plastics. As best seen in FIGS. 10–12, the knuckle slide is made up of a generally cylindrical body 126 with a pair of posts 128 extending laterally outward from the body in opposite directions to fit within elongate windows or slots 130 formed in housing sidewalls 106. One of the housing sidewall windows 130 is provided with a ratchet strip 132 having teeth which engage a notched surface 134 on the corresponding post to permit indexed movement of knuckle slide 124 in the proximal direction relative to the first handle. A pair of buttons 135 are preferably mounted on terminal ends of posts 128 to facilitate movement of the knuckle slide relative to the first handle as described below.

Cylindrical slide body 126 is hollow and includes a beveled proximal end 136, a distal end 138 and a longitudinal channel 140 of cylindrical configuration extending between the proximal and distal ends to receive outer tubular member 12 in telescoping relation. Proximal end 136 of the slide body is beveled to correspond substantially to the angle on the proximal surface of handle housing 102 so that, when the knuckle slide is in the position shown in FIG. 1, proximal ends of the knuckle slide and the handle housing are adjacent one another. An elongate slot 142 is formed through a bottom of slide body 126, looking at FIG. 11, the slot being defined by a pair of longitudinal edges 144 and 146 extending generally in parallel on opposite sides of a central vertical plane 148 of the slide body. The first longitudinal edge 144 of the slot, shown on the right in FIGS. 12–14, extends distally from the proximal end of the slide body to a transverse edge 150 of the slot at a fixed distance from the central vertical plane of the slide. The second longitudinal edge 146, shown on the left in FIGS. 12–14, includes a proximal portion 152 closer to the central vertical plane than the first longitudinal edge and a distal portion 154 about the same distance from the plane as the first longitudinal edge, the proximal and distal edge portions being generally parallel to one another and connected by an angled edge portion 156 oriented at an acute angle θ (e.g., about 30°) relative to the distal direction. First and second longitudinal edges 144 and 146 of the slot are tilted or canted slightly at an angle α (e.g., between about 3° and about 12° counterclockwise looking distally) relative to the central vertical axis or plane of the slide body, with the junction 158 between the second longitudinal edge of the slot and the proximal end of the slide body being chamfered at an acute angle φ (e.g., about 30°) relative to the proximal direction to permit centrally located members (such as the pusher described below) to slide into the canted slot longitudinally and, in so doing, to rotate knuckle slide 124 in a clockwise direction, looking distally, such that the notched post does not engage ratchet strip 132 when the centrally located member is disposed along the proximal portion of the second longitudinal edge.

The bottom surface of knuckle slide 124 is notched to create a cam surface composed of a flat 160 adjacent the proximal end of the slide and a ramp 162 extending downwardly, looking at FIG. 11, from a distal end of the flat at an acute angle (e.g., about 20°) relative to the distal direction. As best seen in FIG. 10, flat 160 corresponds substantially in length to proximal edge portion 152, with ramp 162 being longitudinally aligned with angled edge portion 156.

Inner member 16 is connected to the first handle by pin 44 which, as mentioned above, extends through slots 20 and 22 in the outer tubular member and middle tubular member, respectively. A pin hole 164 is formed through the bottom wall of handle housing 102 in alignment with an opening 165 near the proximal end of inner member 16 for placement of the pin, and knuckle slide 124 includes a distal facing slot 166 configured to receive pin 44 when the slide is in a forward or distal position within the handle housing as shown in FIG. 1.

Referring still to FIGS. 1 and 2, the second or proximal handle 24 includes a pair of laterally spaced, parallel lugs or ears 168 extending upwardly from a finger loop 170. A pin 172 extends perpendicularly through ears 168, slots 26 in the outer tubular member and holes 56 in the middle tubular member to connect the second handle to the middle tubular member while allowing the middle tubular member to slide somewhat within the outer tubular member. Forward edges 174 of the ears are convexly curved to define a cam surface of generally fixed radial dimension relative to pin 172. The lateral spacing between ears 168 corresponds generally to the diameter of outer tubular member 12 so that, when the second handle is brought into contact with the first handle, the ears of the second handle can be made to pivot about pin 172 using the beveled proximal end of knuckle slide 124 as a fulcrum surface without causing the pin to be moved axially within the slot in the outer tubular member a substantial amount. If desired, however, forward edges 174 of the ears can be configured to define a cam surface of increasing radial dimension in the counterclockwise direction, looking at FIG. 1, relative to pin 172 in order to produce proximal movement of the pin within the slot in the outer tubular member when the second handle is moved clockwise.

A pusher 176 carried by the second handle prevents pivotal movement of the second handle until the first and second handles are squeezed together, at which point the second handle can be pivoted to cause the pusher to move the outer tubular member axially relative to the middle tubular member, the amount of axial movement or displacement being controlled by the adjustable stop mounted on the proximal end of the outer tubular member. Referring to FIGS. 15 and 16, pusher 176 includes an arm or bar formed of a thin strip of a relatively rigid material, such as stainless steel, having a proximal end 180 pivotally mounted on a pin 182 within a pocket 184 formed in the second handle and a distal end 186 defining a shoulder 188 and a rearwardly angled locking member or finger 190 extending upwardly (looking at FIG. 16) from the shoulder at an acute angle β (e.g., about 70°) relative to the shoulder. A pair of small cylindrical protrusions or pegs 192 extend laterally outward from opposite sides of the pusher arm below finger 190 to function as cam followers which slide along the bottom surface of knuckle slide 124 as the first and second handles are squeezed together. A bias member, such as the torsion spring 194 shown in FIG. 2, is connected between pusher arm 176 and second handle 24 to bias the pusher in a clockwise direction, looking at FIG. 15, so that finger 190 is normally received within apertures 54 and 78 formed in the middle tubular member and the outer tubular member, respectively, thereby preventing relative axial movement between the tubular members when the handles are sufficiently axially spaced from one another. As best seen in FIG. 16, apertures 54 and 78 tilt rearwardly at the acute angle β relative to the proximal direction to receive finger 190 when shoulder 188 abuts an outer surface of outer tubular member 12. While a bias member in the form of a helical torsion spring is shown, it will be appreciated that any type of bias member can be used including, but not limited to, spiral springs, leaf springs, compression springs and tension springs.

In use, elastic rings 202 are loaded onto the applicator 10 by locking outer and middle tubular members 12 and 14 in a loading position, withdrawing forceps 30 into the middle tubular member, and placing the rings on the distal portion of the middle tubular member in an expanded state. Any suitable rings can be used including, but not limited to, the rings disclosed in U.S. Pat. No. 4,167,188 to Lay, et al., U.S. Pat. No. 4,485,814 to Yoon and 4,548,201 to Yoon, the disclosures of which are incorporated herein by reference. An example of a suitable ring for female sterilization is tubular with an outer diameter of about 0.16 inch, an inner diameter of about 0.04 inch, and a length or width of about 0.10 inch in an undeformed, rest state. Such a ring is preferably made of dimethylpolysiloxane containing 1.6 to 2.0 mg of barium sulfate, with a weight of about 36 mg and opaque white in color. When loaded onto the middle tubular member, such a ring will assume a slightly distorted tubular shape having an outer diameter of about 0.280 inch, an inner diameter of about 0.212 inch, and a length of about 0.065 inch long.

The tubular members can be placed in a loading position by rotating knob 86 until the fin marked "L" is oriented to extend upwardly, looking at FIG. 5, such that stop member 98 abuts the first abutment surface or step 58 at the proximal most end of middle tubular member 14 as shown in FIG. 7. Outer tubular member 12 is thus locked in place with the distal end of middle tubular member 14 protruding from the distal end of the outer tubular member a predetermined distance corresponding substantially to the thickness or width of two rings (e.g., about 0.130 inch). Handles 18 and 24 are also drawn together axially as shown in FIG. 1 such that the forceps 30 is received within middle tubular member 14. With handles 18 and 24 drawn together as shown, pusher arm 176 is lifted away from middle tubular member 14 by knuckle slide 124 such that finger 190 at the distal end of the pusher arm is not received within aperture 54 in the middle tubular member. However, since knob 86 is in the loading position, the middle tubular member is locked or prevented from moving proximally relative to the outer tubular member during the loading procedure by stop member 98.

One loading method, illustrated in FIGS. 17–19, utilizes a conical loader 196 having a circular base 198 of about the same diameter as the middle tubular member and a reduced diameter neck 200 protruding from the base. The method involves inserting the reduced diameter neck of loader 196 into the open distal end of middle tubular member 14 as shown in FIG. 17 until base 198 of the loader abuts the middle tubular member as shown in FIG. 18. An elastic ring 202 is then placed at the tip or apex 204 of the cone (or on a rod extending from the apex of the cone, for example as shown by broken lines in FIG. 17 at 205) and is moved longitudinally along the cone in the direction of increasing diameter as shown in FIG. 18 to cause the ring to slide onto the distal end of middle tubular member 14 in an expanded state. The expanded ring 202 is pushed along the middle tubular member in a proximal direction until it abuts the distal end of outer tubular member 12. Another ring 202' is advanced along conical loader 196 in the same manner and is pushed along middle tubular member 14 in an expanded state until it abuts ring 202, as shown in FIG. 19.

In accordance with the present invention, the applicator 10 can be stabilized during the ring loading procedure by resting the flat proximal face 96 of knob 86 against a flat surface, such as a table top, such that the applicator extends perpendicular to the flat surface without wobbling thereby reducing the risk of dropping a ring or the applicator. Many operations, such as sterilization of females through ligation of the fallopian tubes, require the use of two elastic rings in order to ligate the two tubes. Thus, it will be appreciated that by loading two elastic rings onto the ring applicator the surgeon can perform the entire ligation operation without having to withdraw and reload the ring applicator during surgery.

Ring applicator 10 can be operated with one hand by inserting one or more fingers of the hand through finger loop 104 of the first handle 18 and the thumb of the same hand through finger loop 170 of the second handle 24. In the case of female sterilization, the ring applicator is inserted into the abdominal cavity with forceps 30 retracted and a pair of rings 202 and 202' loaded on the distal portion of middle tubular member 14. The forceps 30 is moved from the retracted position shown in FIG. 1 to the extended position shown in FIG. 15 by moving the second handle 24 proximally relative to the first handle 18. Proximal movement of the second handle 24 causes outer and middle tubular members 12 and 14 to move proximally relative to inner member 16. Inner member 16 does not move axially because pin 44 connecting the first handle 18 to the inner member slides within slots 20 and 22 in the outer and middle tubular members, respectively, as the outer and middle tubular members are moved proximally. Proximal movement of outer and middle tubular members 12 and 14 continues until pin 44 engages or abuts the distal end of the slots, at which point forceps 30 protrudes fully from the distal end of the middle tubular member and assumes the open configuration shown in FIG. 15. As the second handle 24 is moved proximally relatively to the first handle 18, pusher 176 is also withdrawn from knuckle slide 124 and, due to the biasing force of spring 194, the pusher will pivot in a clockwise direction, looking at FIG. 15, causing the finger 190 at the distal end of the pusher to be received within apertures 78 and 54 in the outer and middle tubular members, respectively. As best seen in FIG. 16, shoulder 188 engages the outer surface of outer tubular member 12 to limit the depth of penetration of finger 190 into apertures 54 and 78 so that the finger will not extend beyond the inner surface of middle tubular member 14 in a manner which might interfere with movement of inner member 16 relative to the outer and middle tubular members.

With forceps 30 in the open configuration shown in FIG. 15, a fallopian tube 206 can be positioned in the space between grasping members 32a and 32b in order to be grasped and drawn into middle tubular member 14. It is important that fallopian tube 206 be positioned proximally of the tip of the shorter grasping member 32b before the forceps is closed so that, when the forceps is closed, the tip of the shorter grasping member will not penetrate into the tube. In endoscopic procedures it is often difficult to discern the respective lengths of the grasping members in the image provided by the endoscope and, accordingly, one, or both of the grasping members can be colored to provide a distinguishing characteristic which is easily recognized by the surgeon while remotely viewing the endoscopic image. For example, the shorter grasping member 32b can be colored yellow or green while the longer grasping member 32a is left in its natural grayish silver color as illustrated in FIG. 20 wherein the crisscrossed hatch pattern on the shorter member is meant to denote the color yellow.

With the fallopian tube 206 properly positioned between grasping members 32a and 32b of the forceps 30, the surgeon closes the forceps by moving the first handle 18 in a proximal direction relative to the second handle 24. By so doing, inner member 16 is moved proximally with respect to middle tubular member 14 thereby causing the forceps 30 to close around the fallopian tube 206 as shown in FIG. 21 so that, as the first handle 18 is moved even further proximally, the fallopian tube is bent into a loop or knuckle by the forceps and drawn inside the middle tubular member as shown in FIG. 22. At the same time, pusher 176 is received within slot 142 in knuckle slide 124 causing the pegs 192 on opposite sides of the pusher to slide along the bottom surface of the knuckle slide. Initially, pegs 192 glide along the flat 160 at the proximal end of the slide without affecting the position of finger 190 within apertures 54 and 78. As the pegs 192 slide along ramp 162, however, pusher 176 is pivoted counterclockwise, looking at FIGS. 22 and 23, and is thus lifted away from middle tubular member 14 against the bias of spring 194. The height of ramp 162 is such that the finger 190 at the distal end of pusher 176 is no longer received in the aperture 54 in middle tubular member 14 when the pegs 192 reach the control surface 207 on the distal side of the ramp, thereby permitting relative axial movement between the outer and middle tubular members.

The elastic ring 202' is preferably ejected onto the fallopian tube 206 when the forceps 30 is completely withdrawn into middle tubular member 14. This is easily determined by the surgeon since the length of slots 20 and 22 is such that the proximal surface 1 12 of first handle 18 will contact cam surfaces 174 of second handle 24 when the forceps 30 is completely withdrawn. Since distal tips 70 and 48 of the outer and middle tubular members are transparent, the position or length of the knuckled fallopian tube 206 within the middle tubular member can also be determined directly by visually observing the fallopian tube through the transparent tips using an endoscope inserted into the abdominal cavity through a separate incision or portal. The unobstructed view of the fallopian tube from all angles also permits the condition of the fallopian tube to be determined prior to ejecting a ring.

To adjust the ring applicator 10 for ejection of the first ring, knob 86 is rotated to position stop member 98 in alignment with the second abutment surface or step 60 at the proximal end of middle tubular member 14 as shown in FIGS. 24 and 25. In the case of the knob illustrated herein, this can be accomplished by removing the thumb from finger loop 170 and pushing fins 92 with the thumb to cause the knob to rotate until the fin labeled "1" is oriented to extend upwardly, looking at FIG. 22. When the second handle 24 is squeezed or caused to pivot clockwise, as shown in FIG. 26, pusher 176 will drive outer tubular member 12 distally relative to middle tubular member 14, as shown in FIG. 27, until stop member 98 engages the second abutment surface or step 60, as shown in FIG. 28, to prevent further distal movement of the outer tubular member relative to the middle tubular member. Since the second abutment surface 60 is spaced about one ring width from the first abutment surface 58, the outer tubular member will have moved distally about one ring width (e.g., about 0.065 inch) relative to the middle tubular member thus ejecting the distal most or first ring 202' onto the fallopian tube 206 while leaving enough of the middle tubular member protruding from the outer tubular member to retain the second ring 202 thereon as shown in FIG. 29. Abutment of stop member 98 with the second abutment surface or step 60 at the proximal end of middle tubular member 14 provides the surgeon with a tactile signal that the first ring has been ejected around the fallopian tube. Finger loops 104 and 170 can also be configured to contact one another at this point, for example as shown by broken lines at 170', to provide further tactile feedback to the surgeon.

Without withdrawing ring applicator 10 from the abdominal cavity, second handle 24 is pivoted counterclockwise, looking at FIG. 26, to cause outer tubular member 12 to return to the loading position wherein middle tubular member 14 protrudes distally from the outer tubular member about two ring widths and apertures 54 and 78 are aligned. First handle 18 is then moved distally relative to second handle 24 to eject the occluded fallopian tube 206 from middle tubular member 14 by causing the forceps 30 to move distally relative to the middle tubular member until the grasping members are free to spring open as shown in FIG. 30 thereby releasing the fallopian tube. As the first handle 18 is moved distally, pusher 176 is released from knuckle slide 124 and will pivot clockwise, looking at FIG. 30, under the influence of spring 194 causing finger 190 at the distal end of the pusher to project inwardly into the aperture 54 in the middle tubular member as described above.

Figure 35:
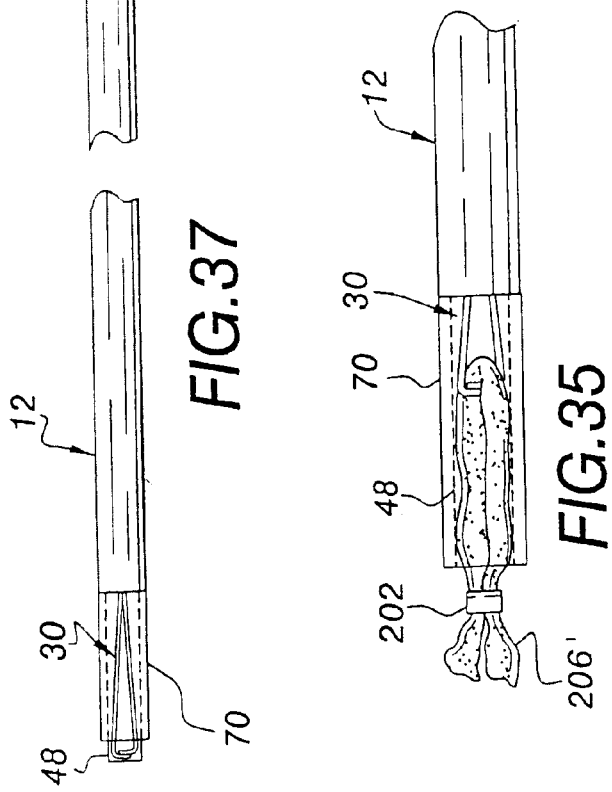
FIG. 35 is a fragmentary side view of the distal end of a ring applicator according to the present invention after a second elastic ring has been ejected onto a fallopian tube.
Figure 36:
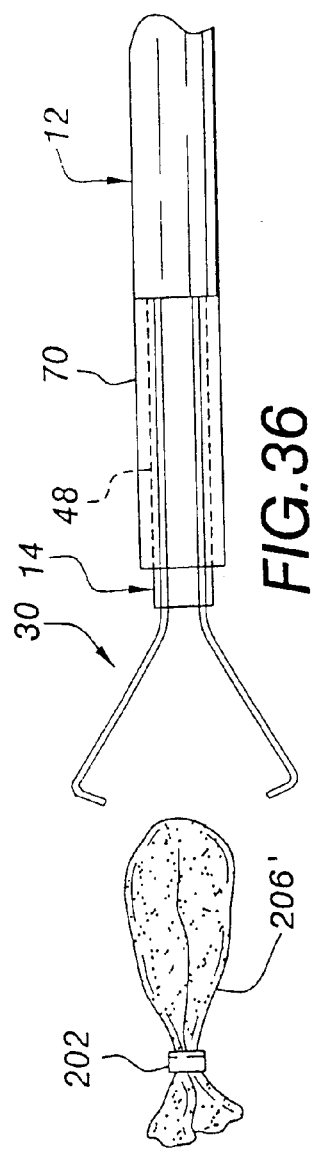
FIG. 36 is a fragmentary side view of the distal end of a ring applicator according to the present invention after the second occluded fallopian tube has been ejected from the ring applicator.

To adjust the ring applicator 10 for placement of the second ring 202, knob 86 is rotated to position the stop member 98 in alignment with the third abutment surface or step 62 at the proximal end of middle tubular member 14 as shown in FIGS. 31 and 32. In the case of the knob illustrated herein, this is accomplished by rotating the knob with the thumb until the fin labeled "2" is oriented to extend upwardly, looking at FIG. 30. Since middle tubular member 14 is still in the loading position, the axial distance between stop member 98 and the third abutment surface is about two ring widths. The other fallopian tube 206' is then located, positioned between the grasping members, and drawn into middle tubular member 14 as shown in FIG. 33 by sliding the first handle 18 proximally until it abuts the second handle 24 in the manner described above. The pusher 176 engages knuckle slide 124 in the first handle housing 102, releasing middle tubular member 14 from the pusher. As the second handle 24 is squeezed, movement of pusher 176 causes outer tubular member 12 to move distally relative to middle tubular member 14. Knob 86 at the proximal end of outer tubular member 12 is also caused to move distally relative to middle tubular member 14 until stop member 98 abuts the third abutment surface or step 62 at the proximal end of the middle tubular member as shown in FIG. 34. At this point, outer tubular member 12 has moved about two ring widths into distal alignment with middle tubular member 14 thereby pushing the second ring 202 over the edge of the middle tubular member onto the fallopian tube 206' as shown in FIG. 35. As mentioned above, the feeling of stop member 98 abutting the third abutment surface or step 62 at the proximal end of middle tubular member 14, or of finger loops 104 and 170 contacting one another, signals the surgeon that the second ring has been ejected around the fallopian tube 206'. The second handle 24 is then rotated counterclockwise, looking at FIG. 30, to return the middle and outer tubular members 14 and 12 to the loading position, and first handle 18 is moved distally relative to the second handle to expel the second fallopian tube 206' from the applicator as shown in FIG. 36 in the same manner as described above. When both fallopian tubes are occluded, the operation is completed by withdrawing the applicator from the body and closing any incisions.

Figure 37:
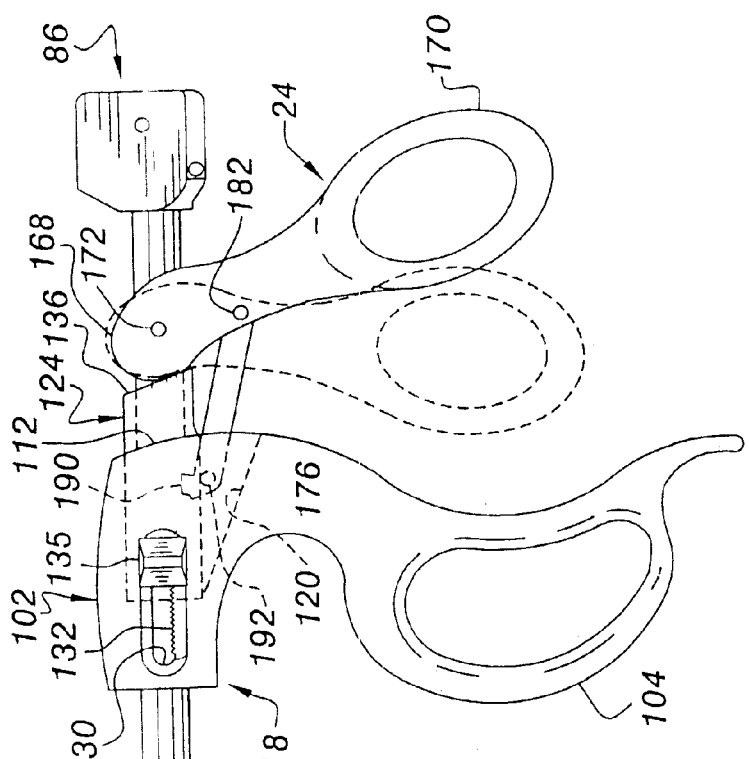
FIG. 37 is a side view, broken longitudinally, of a ring applicator according to the present invention illustrating use of a knuckle slide to pre-release an elastic ring.

The ring applicator according to the present invention can also be used to eject an elastic ring onto anatomical tissue structures, such as polyps, when the forceps have not been completely withdrawn into the middle tubular member. In this case, the first handle 18 is moved proximally to a position longitudinally spaced from the second handle 24 as shown in FIG. 37 such that the handles do not abut one another and the forceps 30 is only partly withdrawn into middle tubular member 14. The pusher 176 is thus prevented from engaging knuckle slide 124 in handle housing 102 to release the middle tubular member and allow relative axial movement between the outer and middle tubular members. Pivotal movement of second handle 24 is also affected by depriving the second handle of the fulcrum surface defined by proximal surface 112 of the first handle. Ordinarily it would be impossible to eject a ring prematurely under these conditions, however, the present invention overcomes this limitation by allowing knuckle slide 124 to move proximally relative to handle housing 102 and into contact with second handle 24. The knuckle slide 124 is moved by grasping buttons 135 on either side of the knuckle slide and pulling back on the knuckle slide to cause posts 128 of the knuckle slide to slide within the windows 130 in the handle housing. One of the posts 128 is configured to engage ratchet strip 132 as it is moved so that, once positioned, knuckle slide 124 will tend not to move out of position until unlocked in the manner described below. The knuckle slide 124 is moved proximally until proximal end 136 of the knuckle slide abuts second handle 24. At this point, pusher 176 has been received by proximal slot 142 in the knuckle slide and has been lifted away from middle tubular member 14 allowing relative axial movement between the outer and middle tubular members. With upper ends or ears 168 of the second handle resting against the beveled proximal end surface 136 of knuckle slide 124, the second handle can be pivoted in the usual manner to cause outer tubular member 12 to move distally relative to middle tubular member 14 to eject a ring. The first handle 18 can then be moved distally as described above to eject the occluded anatomical tissue structure from the middle tubular member and to release pusher from the knuckle slide.

Knuckle slide 124 can be automatically reset to its original position within the first handle housing 102 by simply moving second handle 24 distally against the knuckle slide without pivoting the second handle. As the pusher 176 moves distally it contacts the chamfer 158 at the proximal end of slot 142 in the knuckle slide 124 imparting torsional forces which cause the knuckle slide to rotate or twist slightly (e.g., between about 3° and about 12°) in a clockwise direction, looking distally. Clockwise rotation of knuckle slide 124 causes the notched post 128 to lift away from ratchet strip 132 thereby allowing the knuckle slide to move distally relative to handle housing 102. The knuckle slide 124 remains in a rotated or unlocked position so long as the pusher 176 is disposed along the proximal portion 152 of the second longitudinal edge 146. As a result, distal forces applied to knuckle slide 124 without rotating second handle 24 will cause the knuckle slide to move back into the housing with little or no resistance from ratchet strip 132. The knuckle slide 124 will rotate back to its locked position engaging ratchet strip 132 when the second handle 24 is pivoted to cause the pusher 176 to slide along the ramp 162 onto the control surface 207 on the distal side of the ramp or when the pusher is completely removed from the slot in the knuckle slide.

An insulated connector or plug, shown by broken lines in FIG. 1 at 208, can optionally be mounted on handle housing 102 opposite finger loop 104 or at any other convenient or suitable location on the ring applicator to connect with electrically conductive elements of the ring applicator for performing unipolar or bipolar electric coagulation, for example using one or both of the grasping members 32*a* and 32b as conductive elements. Plug 208 is shown mounted on a pin 209 to permit pivotal movement of the plug between an upright position where the plug is operational and a folded position where the plug is received within a recess in the handle housing in an unobtrusive manner for storage. A modification of a ring applicator according to the present invention wherein the forceps is specifically configured to occlude anatomical tissue and/or take down adhesions by application of electrical energy is illustrated in FIG. 38.

While forceps in the form of opposed grasping members have been described, it will be appreciated that the term "forceps" is intended to include any type of grasping or holding device. For example, the forceps could include a device which draws tissue into a tubular member using suction. When the forceps includes opposed grasping members, the grasping members can be mounted at the distal end of a solid rod as shown or the grasping members can be mounted at the distal end of a hollow rod defining an operating channel through the ring applicator. For example, in FIG. 39, a modification of a forceps for use with a ring applicator according to the present invention is shown wherein the modified forceps 30 includes a pair of grasping members 32a and 32b extending distally from the distal end of a hollow tubular rod 28 of circular cross-section defining an operating channel 213 through which instruments such as endoscopes, cutters, needles and the like can be introduced via the port 101 at the operative site. As mentioned above, it is important that the shorter grasping member be used to snag anatomical tissue structures to avoid puncturing the tissue. In FIG. 40, a modification of a grasping member is shown wherein the tip 41 of the grasping member 32 is configured with a ball 215 at a terminal end to contact anatomical tissue in an a traumatic manner. Other atraumatic shapes can be used including, but not limited to, hemispherical, ovoid, disk-like and tear drop shapes.

The forceps can be formed with the rod as an integral one-piece unit or the forceps can be formed separately and joined with the rod in any suitable manner dependent upon the materials used. In FIG. 41, a modified inner member 16 is shown wherein the forceps 30 includes a coupling 216 configured to mate cooperatively with the distal end of a hollow, tubular rod 28 to permit easy removal and replacement of the forceps in an interchangeable manner. Coupling 216 includes a hollow, cylindrical neck 218 of reduced diameter at a proximal end provided with external threads 220 which engage internal threads 222 formed on an inner surface of the hollow, tubular rod to permit repeated attachment and detachment of the forceps in a rapid and non-destructive manner. FIGS. 42 and 43 illustrate other couplings 216 which can be used to detachably connect forceps 30 with a tubular rod 28 according to the present invention. In FIG. 42, the distal end of the tubular rod 28 is provided with circumferentially spaced openings or apertures 224 and the neck 218 of the coupling 216 includes corresponding detents 226 which deform inwardly to permit insertion of the coupling into the distal end of the tubular rod and thereafter spring outwardly into the openings or apertures to lock the forceps in place. The coupling shown in FIG. 43 is similar to that shown in FIGS. 41 and 42; however, the neck 218 is configured to engage the inner surface of the tubular rod to form a friction fit. Similar couplings can be used to detachably connect forceps with solid rods having recesses or other mating features at a distal end. It will also be appreciated that a neck can be formed at the distal end of the rod and connected to the forceps in a similar manner.

The forceps 30 illustrated in FIGS. 41 and 43 each have a different number of grasping members 32. More specifically, two grasping members 32 are shown in FIG. 41, three grasping members 32 are shown in FIG. 42, and four grasping members 32 are shown in FIG. 43. While these forceps are detachable, it will be appreciated that any of the forceps described herein can be modified to include any number of grasping members dependent upon the procedure to be performed. Alternatively, or in addition to making the forceps detachable, a proximal end of the rod 28 can be configured to detach from other components 228 of the ring applicator in a similar manner, for example by providing the proximal end of the rod with a reduced diameter neck 218 having external threads 220 as shown in FIG. 44. This allows the entire inner member to be replaced as a unit if desired. The forceps shown in FIGS. 42 and 43 are particularly useful in grasping polyps, it being noted that if a polyp bursts when grasped, the present invention allows placement of a ring.

Figure 45:
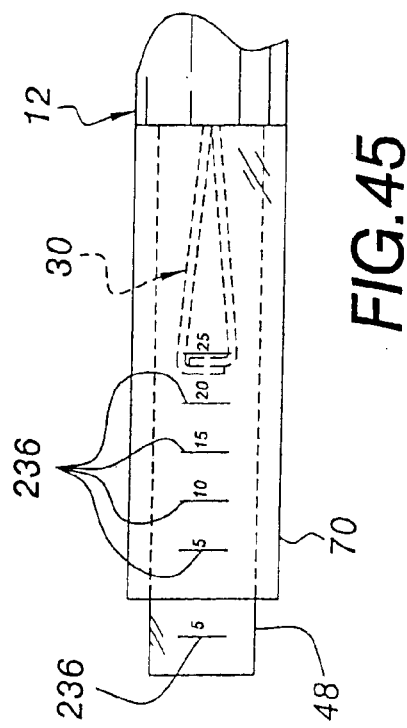
FIG. 45 is a fragmentary side view of the distal end of the ring applicator illustrating scale markings.

When the forceps is used to retract anatomical tissue into the middle tubular member, it is desirable to accurately determine the length of tissue contained within the middle tubular member prior to ejecting an elastic band. By providing transparent tips for the outer and middle tubular members, the ring applicator of the present invention allows the surgeon to visually observe the tissue within the middle tubular member from virtually any angle, for example using an endoscope positioned at the operative site through a separate incision. In FIG. 45, a modification of a ring applicator according to the present invention is shown wherein a scale is imprinted or otherwise formed on one or both of the transparent tips 48 and 70 to assist the surgeon in determining the length of the anatomical tissue structure contained within middle tubular member 14. Each scale consists of spaced markings 236 indicative of a unit of measurement such as inches or centimeters. In use, a surgeon can refer to the scale markings 236 for a measurement when an anatomical tissue structure has been retracted into the middle tubular member. If the middle tubular member 14 protrudes from the outer tubular member 12, the distance from the distal end of the middle tubular member to the distal end of the outer tubular member can be determined from the scale on the middle tubular member and subsequently added to the distance from the distal end of the outer tubular member to the tip of the anatomical tissue structure as determined using the scale on the outer tubular member. Thus, for example, if an excessively fat or bulky fallopian tube cannot be retracted fully into the middle tubular member, the surgeon may check the scales to determine whether the knuckle is of sufficient length to be occluded using an elastic band. Forming the scale markings on the transparent tips allows accurate measurement of the tissue within the middle tubular member by direct visual comparison, thereby eliminating the estimating errors which can occur when no scale is available, when a scale is misaligned with the tube, or when the surgeon does not have a complete view of the tissue within the middle tubular member.

The outer tubular member can have any suitable configuration in cross-section to fit through a portal formed in the wall of an anatomical cavity and to receive the middle tubular member for sliding movement therein including, but not limited to, elliptical and polygonal cross-sectional configurations. Further, respective outer surfaces of the outer and middle tubular members can be of different cross-sectional configuration than their respective inner surfaces. The inner member can be hollow or solid and have any suitable cross-sectional configuration to slide within the middle tubular member. Distal ends of the inner member, the outer tubular member and/or the middle tubular member can be made of flexible materials which are bendable.

Figure 46:
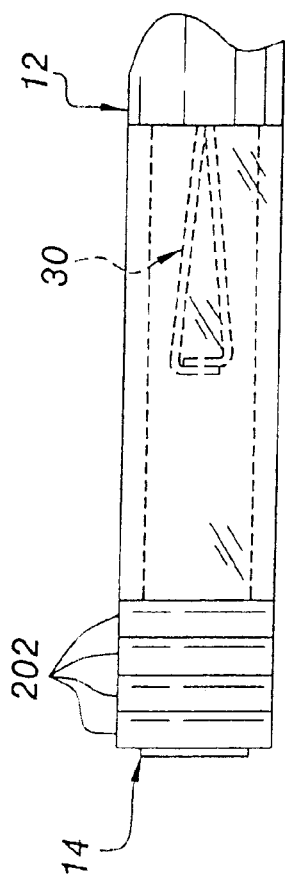
FIG. 46 is a fragmentary side view of the distal end of the ring applicator illustrating four elastic rings mounted on the middle tubular member.

The ring applicator, according to the present invention, can be used to place a single occlusion ring about a single anatomical tissue structure, or a plurality of occlusion rings about the same or different anatomical tissue structures. Thus, while the ring applicator has been described for use in applying two occlusion rings, it will be appreciated that one or more than two rings may be applied. In FIG. 46, for example, four elastic rings 202 are shown in an expanded state on middle tubular member 14. Dependent upon the width of the rings and the spacing between abutment surfaces at the proximal end of the middle tubular member, rings 202 can be ejected individually, in pairs, or all at once.

Although the ring applicator according to the present invention is particularly useful for performing female sterilization procedures involving the fallopian tubes, it can be used to apply rings to the vas deferens in male sterilization procedures, and to other anatomical tissue structures such as polyps and hemorrhoids.

Figure 47:
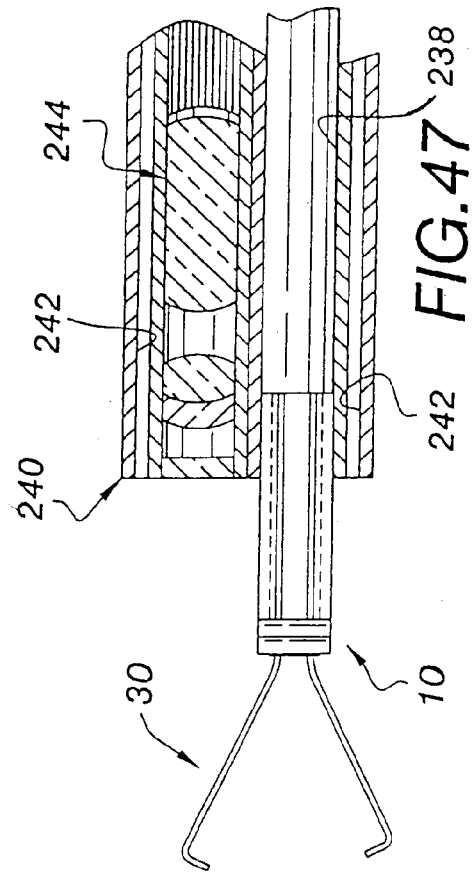
FIG. 47 is a fragmentary sectional side view of a ring applicator according to the present invention inserted through an endoscope.

In FIG. 47, a ring applicator 10 according to the present invention is shown extending through a channel 238 formed in an endoscope 240. Endoscope 240 can be flexible or rigid and may have additional channels 242 defined therethrough. Preferably, the endoscope optics 244 are laterally offset from the operating channel 238 to permit visualization of the ring applicator forceps 30 when extended. Conventional or digital (e.g., CCD) optics can be used.

Although the ring applicator according to the present invention has been described as including a knuckle slide which allows elastic rings to be applied to anatomical tissue structures which have not been fully retracted into the middle tubular member, it will be appreciated that the ring applicator can be provided without a knuckle slide if desired.

The ring applicator according to the present invention can be configured for easy disassembly to facilitate sterilization for reuse. Alternatively, the ring applicator can be provided as a disposable unit. If desired, some of the components of the ring applicator can be disposable while others are sterilized for reuse. The components can be made of multiple parts of various configurations and materials to reduce cost and/or simplify fabrication. The ring applicator can have various valves, stop cocks and seals in the handle housing and/or inner member to control fluid flow therethrough.

The features of the various embodiments described above can be combined in any manner desired dependent upon the operational requirements of the procedure to be performed and the complexity of the ring applicator.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A ring applicator for applying elastic rings to anatomical tissue during surgical procedures comprising:
    an outer tubular member having proximal and distal ends;
    a middle tubular member movably disposed within said outer tubular member, said middle tubular member including a distal portion configured to hold an elastic ring in an expanded state and a proximal portion with a plurality of longitudinally spaced abutment surfaces;
    an elongate inner member movably disposed within said middle tubular member and including a forceps at a distal end; and
    an adjustable stop mechanism mounted on said proximal end of said outer tubular member and including a stop member movable relative to said outer tubular member between a plurality of stop positions, said stop member being aligned with a different abutment surface in each stop position to limit axial movement of said outer tubular member relative to said middle tubular member.

2. A ring applicator as recited in claim 1 wherein said longitudinally spaced abutment surfaces are defined by notches at a proximal end of said middle tubular member.

3. A ring applicator as recited in claim 2 wherein said adjustable stop mechanism includes a knob rotatably mounted on said proximal end of said outer tubular member and carrying said stop member.

4. A ring applicator as recited in claim 3 wherein said knob defines a bore of generally circular cross-section receiving said proximal end of said outer tubular member and wherein said stop member includes a pin extending across said circular cross-section of said bore.

5. A ring applicator as recited in claim 4 wherein three abutment surfaces are formed at 120° intervals about said proximal end of said middle tubular member and wherein said pin transacts an arc of about 120° across said bore so as to abut each of said abutment surfaces individually in said stop positions.

6. A ring applicator as recited in claim 3 wherein the knob has a flat proximal face.

7. A ring applicator as recited in claim 1 wherein said longitudinal spacing between said abutment surfaces is about one ring width.

8. A ring applicator as recited in claim 7 wherein said stop member abuts a first of said abutment surfaces when in a first of said stop positions such that said middle tubular member is locked in a loading position wherein a distal end of said middle tubular member protrudes distally from said outer tubular member to receive an elastic ring without moving axially relative to said outer tubular member.

9. A ring applicator as recited in claim 8 wherein said distal end of said middle tubular member protrudes distally from said outer tubular member a distance approximately equal to the width of two elastic rings when said middle tubular member is in said loading position.

10. A ring applicator as recited in claim 7 wherein said stop member is axially movable about one ring width relative to a second of said abutment surfaces when in a second of said stop positions.

11. A ring applicator as recited in claim 10 wherein said stop member is axially movable about two ring widths relative to a third of said abutment surfaces when in a third of said stop positions.

12. A ring applicator as recited in claim 11 and further comprising a distal handle connected with said inner member and a proximal handle connected with said middle tubular member within reach of said knob to permit one-handed operation of said handles and said knob.

13. A ring applicator as recited in claim 12 wherein said knob includes markings correlating stop positions of said stop member with rotational positions of said knob relative to said outer tubular member.

14. A ring applicator as recited in claim 12 wherein said knob includes outwardly extending fins configured to assist in rotating said knob to place said stop member in a desired stop position.

15. A ring applicator for applying elastic rings to anatomical tissue during a surgical procedure comprising:
    an outer tubular member having an aperture formed therein;

a middle tubular member movably disposed within said outer tubular member and having an aperture formed therein;

an elongate inner member movably disposed within said middle tubular member, said inner member including a forceps at a distal end;

a distal handle connected to said inner member via slots in said outer and middle tubular members;

a proximal handle pivotally connected to said middle tubular member via a slot in said outer tubular member; and a pusher having a proximal end pivotally connected with said proximal handle and a distal end movable between a latched position where said distal end of said pusher protrudes into said apertures to prevent pivotal movement of said proximal handle and relative axial movement between said outer and middle tubular members, and an unlatched position where said distal end of said pusher is disengaged from said aperture in said middle tubular member to permit pivotal movement of said proximal handle in order to move said outer tubular member axially relative to said middle tubular member.

16. A ring applicator as recited in claim 15 wherein a cam surface with a ramp is defined in said distal handle and said pusher includes a cam follower which slides along said cam surface when said handles are moved toward one another, said pusher becoming disengaged from said middle tubular member when said cam follower slides along said ramp.

17. A ring applicator as recited in claim 16 wherein said cam surface is defined by a knuckle slide movably disposed in said distal handle.

18. A ring applicator as recited in claim 17 wherein said knuckle slide includes a main body defining a central bore for receiving said outer tubular member and a post extending outwardly from said main body through a window formed in said distal handle.

19. A ring applicator as recited in claim 18 wherein said post is notched, and said ring applicator further comprises a ratchet strip disposed within said window to mate cooperatively with the notches of said post.

20. A ring applicator as recited in claim 19 wherein said slide body includes a slot canted at an angle relative to a central vertical plane of said slide to receive said pusher in a manner causing said knuckle slide to twist in a direction opposite said ratchet so that said knuckle slide can be moved.

21. A ring applicator as recited in claim 15 wherein said proximal handle has forward surfaces of curved configuration and said distal handle has rearward surfaces of beveled configuration against which said curved forward surfaces pivot when said handles are moved together.

22. A ring applicator as recited in claim 21 and further comprising, a knuckle slide with a beveled rearward surface disposed within said distal handle, said knuckle slide being movable relative to said distal handle between a rest position where said rearward surface of said slide is substantially flush with a rearward surface of said distal handle and a retracted position where said rearward surface of said slide protrudes proximally from said rearward surface of said distal handle to permit said proximal handle to pivot when said proximal and distal handles are axially spaced relative to one another.

23. A ring applicator for applying elastic rings to anatomical tissue in surgical procedures comprising:

an outer tubular member having proximal and distal ends;

a middle tubular member movably disposed within said outer tubular member, said middle tubular member having a distal end configured to receive an elastic ring in an expanded condition and a proximal end; and an elongate inner member movably disposed within said middle tubular member and including a pair of opposed grasping members at a distal end, said grasping members including pivot arms of unequal length with distal tips oriented transverse to said arms such that one of said tips is disposed proximally of the other tip when said grasping members are in a closed condition, wherein at least a portion of one of said grasping members has a color allowing said one grasping member to be visually distinguished from the other grasping member when said grasping members are viewed remotely via an endoscope.

24. A ring applicator as recited in claim 23 wherein substantially the entire outer surface of said one grasping member has a color distinguishing said one grasping member from the other grasping member.

25. A ring applicator for applying elastic rings to anatomical tissue in surgical procedures comprising:

an outer tubular member having proximal and distal ends;

a middle tubular member movably disposed within said outer tubular member, said middle tubular member having a distal portion configured to receive an elastic ring in an expanded condition and a proximal portion; and an elongate inner member movably disposed within said middle tubular member and including a forceps at a distal end for grasping anatomical tissue and drawing the tissue into said middle tubular member;

wherein said outer tubular member and said middle tubular member include respective transparent distal portions for viewing anatomical tissue drawn into said middle tubular member, and wherein at least one of said outer tubular member and said middle tubular member include scale markings on the respective transparent distal portion.

26. A ring applicator for applying elastic rings to anatomical tissue during surgical procedures comprising:

an outer tubular member having proximal and distal ends;

a middle tubular member movably disposed within said outer tubular member, said middle tubular member having a distal portion configured to receive an elastic ring in an expanded condition and a proximal portion;

an elongate inner member movably disposed within said middle tubular member and having a forceps at a distal end movable between an extended position where said forceps protrudes from said middle tubular member in an open configuration, and a retracted position where said forceps is disposed within said middle tubular member in a closed configuration;

a distal handle connected to said inner member via slots in said outer and middle tubular members; and a proximal handle pivotally connected to said middle tubular member via a slot in said outer tubular member;

wherein said proximal and distal handles are axially movable relative to one another to cause said forceps to move between said retracted and extended positions relative to said middle tubular member, and wherein said proximal handle is pivotably movable relative to said tubular members when said handles are drawn together to cause said outer and middle tubular members to move relative to one another such that an elastic ring mounted on a distal end of said middle tubular member is ejected.

27. A method of applying elastic rings to anatomical tissue during surgical procedures using a ring applicator having a middle tubular member disposed within an outer tubular member, and an inner member with forceps disposed within the middle tubular member, said method comprising the steps of:

positioning the middle tubular member to protrude distally from the outer tubular member;

adjusting a stop mechanism on the proximal end of the outer tubular member to position a stop member against a first of a plurality of longitudinally spaced abutment surfaces along a proximal portion of the middle tubular member such that the middle tubular member is prevented from moving axially relative to the outer tubular member;

loading an elastic ring onto a distal portion of the middle tubular member;

inserting the ring applicator into the body;

grasping a first anatomical tissue structure using the forceps;

pulling the first anatomical tissue structure into the middle tubular member;

adjusting the stop mechanism on the proximal end of the outer tubular member to position the stop member proximally of a second abutment surface along the proximal portion of the middle tubular member so that the outer tubular member can move axially about one ring width relative to the middle tubular member;

ejecting the elastic ring by moving the outer tubular member distally relative to the middle tubular member until the stop member contacts the second abutment surface; and releasing the first anatomical tissue structure from the middle tubular member.

28. A method of applying elastic rings to anatomical tissue as recited in claim 27 wherein said loading step includes loading a plurality of elastic rings onto the distal portion of the middle tubular member and further comprising the steps of:

grasping a second anatomical tissue structure using the forceps;

drawing the second anatomical tissue structure into the middle tubular member;

adjusting the stop mechanism on the proximal end of the outer tubular member to position the stop member proximally of a third abutment surface along the proximal portion of the middle tubular member such that the outer tubular member can move axially about two ring widths relative to the middle tubular member;

ejecting a second elastic ring from the distal end of the middle tubular member onto the second anatomical tissue structure by moving the outer tubular member distally relative to the middle tubular member until the stop member contacts the third abutment surface; and releasing the second anatomical tissue structure from the middle tubular member.

29. A method of applying elastic rings to anatomical tissue structures during surgical procedures using a ring applicator having a middle tubular member disposed within an outer tubular member and connected to a proximal handle, and an inner member with forceps disposed within the middle tubular member and connected to a distal handle, said method comprising the steps of:

positioning the middle tubular member in a loading position where a distal end of the middle tubular member protrudes distally from the outer tubular member;

locking the middle tubular member in the loading position;

moving the forceps to a retracted position within the middle tubular member by sliding the proximal and distal handles together such that the handles abut one another;

loading an elastic ring onto a distal portion of the middle tubular member;

inserting the ring applicator into the body;

moving the forceps to an extended position protruding from the middle tubular member by sliding the proximal and distal handles apart such that the handles are axially spaced from one another;

positioning the forceps around a first anatomical structure;

pulling the first anatomical tissue structure into the middle tubular member with the forceps by sliding the proximal and distal handles together such that the handles abut one another;

unlocking the middle tubular member so that the outer and middle tubular members can move axially relative to one another; and ejecting the elastic ring onto the first anatomical structure by pivoting the proximal handle about the point of contact between the handles to cause the outer tubular member to move distally relative to the middle tubular member.

30. A method of applying elastic rings to anatomical tissue structures as recited in claim 29 wherein the middle and outer tubular members include apertures which are aligned in the loading position and wherein said step of locking the middle tubular member in the loading position includes placing a locking member in the apertures to prevent axial movement of the middle and outer tubular members relative to one another.

31. A method of applying elastic rings to anatomical tissue structures recited in claim 30 wherein said unlocking step includes removing the locking member from at least one of the apertures to permit axial movement of the middle and tubular members relative to one another.

32. A method of applying elastic rings to anatomical tissue structures as recited in claim 31 wherein the locking member is carried by a pusher arm pivotally connected to the proximal handle and wherein said unlocking step includes the steps of receiving the pusher arm in a cavity defined in the distal handle when the handles are moved towards one another and causing the arm to pivot away from the middle tubular member.

33. A method of applying elastic rings to anatomical tissue structures as recited in claim 32 wherein the locking member remains in the aperture in the outer tubular member following said unlocking step and wherein said ejecting step includes the step of using the arm to push the outer tubular member distally in response to pivotal movement of the proximal handle.

34. A method of applying elastic rings to anatomical tissue structures during surgical procedures using a ring applicator having a middle tubular member disposed within an outer tubular member and connected to a proximal handle, and an inner member with forceps disposed within the middle tubular member and connected to a distal handle, said method comprising the steps of:

positioning the middle tubular member in a loading position where a distal end of the middle tubular member protrudes distally from the outer tubular member;

locking the middle tubular member in the loading position;

moving the forceps to a retracted position within the middle tubular member by sliding the proximal and distal handles together such that the handles abut one another;

loading an elastic ring onto a distal portion of the middle tubular member;

inserting the ring applicator into the body via an incision;

moving the forceps to an extended position protruding from the middle tubular member by sliding the proximal and distal handles apart such that the handles are axially spaced from one another;

positioning the forceps around a first anatomical structure;

pulling the first anatomical tissue structure into the middle tubular member with the forceps by sliding the proximal and distal handles together such that the handles are axially spaced a small distance apart;

moving a knuckle slide disposed within the distal handle proximally relative to the distal handle such that a proximal surface of the knuckle slide abuts the proximal handle;

unlocking the middle tubular member so that the outer and middle tubular members can move axially relative to one another;

ejecting the elastic ring onto the first anatomical structure by pivoting the proximal handle about the point of contact between the proximal handle and the knuckle slide to cause the outer tubular member to move distally relative to the middle tubular member.

35. A method of applying elastic rings to anatomical tissue structures as recited in claim 34 wherein said locking step includes pinning the middle and outer tubular members together using a locking member carried by an arm pivotally connected to the proximal handle and said step of unlocking the middle tubular member includes forcing the arm to pivot away from the middle tubular member as the knuckle slide is moved proximally relative to the proximal handle.

36. A method of applying elastic rings to anatomical tissue structures as recited in claim 35 wherein the knuckle slide includes a cam surface and said unlocking step includes guiding a cam follower on the arm along the cam surface to cause the arm to pivot away from the middle tubular member.

37. A method of applying elastic rings to anatomical tissue structures as recited in claim 34 wherein the knuckle slide engages a ratchet preventing distal movement of the knuckle slide relative to the distal handle and further comprising the step of resetting the knuckle slide by causing the knuckle slide to rotate out of engagement with the ratchet and pushing the knuckle slide back into the distal handle.

38. A method of applying elastic rings to anatomical tissue structures as recited in claim 37 wherein a slot is formed in the knuckle slide at a slight angle relative to the central plane of the slide and wherein said resetting step includes sliding an arm carried by the proximal handle through the slot to cause the knuckle side to rotate out of engagement with the ratchet.

39. A method of applying elastic rings to anatomical tissue structures during surgical procedures using a ring applicator having a middle tubular member disposed within an outer tubular member, an elastic ring mounted on a distal portion of the middle tubular member, and an inner member with a forceps disposed within the middle tubular member, the forceps having opposed grasping members of unequal length and of different color, said method comprising the steps of:

inserting a distal end of the ring applicator into a body cavity;

spreading the grasping members apart;

observing the color of the grasping members to determine which grasping member is shorter;

positioning the anatomical tissue proximally of the tip of the shorter grasping member;

grasping the anatomical tissue using the forceps;

pulling the anatomical tissue into the middle tubular member using the forceps; and ejecting a ring from the middle tubular member onto the anatomical tissue by moving the outer tubular member distally relative to the middle tubular member.

40. A method of applying elastic rings to anatomical tissue structures during surgical procedures using a ring applicator having a middle tubular member disposed within an outer tubular member, an elastic ring mounted on a distal portion of the middle tubular member, and an inner member with a forceps disposed within the middle tubular member, the outer and middle tubular members each having transparent distal tips, said method comprising the steps of:

inserting the ring applicator into a body cavity;

grasping an anatomical tissue structure using the forceps;

pulling the anatomical tissue structure into the middle tubular member using the forceps;

viewing the anatomical tissue structure through the transparent tips of the outer and middle tubular members;

determining whether a desired length of the anatomical tissue structure is pulled into the middle tubular member based upon scale markings on one or both of the transparent tips; and when the desired length is determined, ejecting a ring from the middle tubular member onto the anatomical tissue by moving the outer tubular member distally relative to the middle tubular member.

* * * * *